United States Patent
Zhang et al.

(10) Patent No.: US 12,384,798 B2
(45) Date of Patent: Aug. 12, 2025

(54) ACC INHIBITOR AND USE THEREOF

(71) Applicant: NANJING RUIJIE PHARMA CO., LTD., Jiangsu (CN)

(72) Inventors: Junbo Zhang, Jiangsu (CN); Shuhao Zhu, Jiangsu (CN); Xiaoxin Qi, Jiangsu (CN)

(73) Assignee: NANJING RUIJIE PHARMA CO., LTD, Jiangsu (CN)

( * ) Notice: Subject to any disclaimer, the term of this patent is extended or adjusted under 35 U.S.C. 154(b) by 668 days.

(21) Appl. No.: 17/774,489

(22) PCT Filed: Nov. 6, 2020

(86) PCT No.: PCT/CN2020/127077
§ 371 (c)(1),
(2) Date: May 5, 2022

(87) PCT Pub. No.: WO2021/088980
PCT Pub. Date: May 14, 2021

(65) Prior Publication Data
US 2023/0002405 A1  Jan. 5, 2023

(30) Foreign Application Priority Data

Nov. 7, 2019 (CN) .......................... 201911081908.9

(51) Int. Cl.
*C07D 495/04* (2006.01)
*A61K 9/00* (2006.01)

(52) U.S. Cl.
CPC .......... *C07D 495/04* (2013.01); *A61K 9/0019* (2013.01); *A61K 9/0053* (2013.01); *C07B 2200/07* (2013.01)

(58) Field of Classification Search
None
See application file for complete search history.

(56) References Cited

U.S. PATENT DOCUMENTS

| | | | | |
|---|---|---|---|---|
| 10,995,099 | B2 * | 5/2021 | Zhang | .................. C07D 405/12 |
| 11,186,587 | B2 * | 11/2021 | Wang | .................. A61K 31/519 |
| 2020/0165265 | A1 | 5/2020 | Wang et al. | |

FOREIGN PATENT DOCUMENTS

| | | |
|---|---|---|
| CN | 104105485 B | 10/2014 |
| CN | 106905346 A | 6/2017 |
| CN | 108699078 A | 10/2018 |
| CN | 109305976 A | 2/2019 |
| CN | 111484504 A | 8/2020 |
| WO | WO2013071169 A1 | 5/2013 |
| WO | WO2017151816 | 9/2017 |
| WO | WO 2019/020041 A1 | 1/2019 |
| WO | WO2019015583 | 1/2019 |
| WO | WO2019015583 A1 | 1/2019 |
| WO | WO 2020103851 A1 | 5/2020 |

OTHER PUBLICATIONS

H. James Hardwood Jr.: "Treating the Metabolic Syndrome: Acetyl-CoA carboxylases Inhibition" Expert Opinion Ther Targets. Apr. 2005 vol. 9(2) pp. 267-281.
Stephen M. Berge, et al.: "Pharmaceutical Salts" J Pharm Sci. Jan. 1977 vol. 66(1) pp. 1-19.
Liang Tong, et al.: "Acetyl-coenzyme A carboxylases: versatile targets for drug Discovery" J Cell Biochem. Dec. 15, 2006vol. 99(6) pp. 1476-1488.
Lutfi Abu-Elheiga, et al.: "Mutant mice lacking acetyl-CoA carboxylase 1 are embryonically lethal" Proc Natl Acad Sci Aug. 23, 2005 vol. 102(34) pp. 12011-6.
Jie-Fei Cheng, et al.: "Synthesis and Structure-Activity Relationship of Small-Molecule Malonyl Coenzyme A Decarboxylase Inhibitors" J Med Chem. Mar. 9, 2006 vol. 49(5) pp. 1517-1525.
Lutfi Abu-Elheiga, et al.: "Acetyl-CoA carboxylase 2 mutant mice are protected against obesity and diabetes induced by high-fatyhigh-carbohydrate diets" Proc Natl Acad Sci Sep. 2, 2003 vol. 100(18) pp. 10207-10212.
David B. Savage, et al.: "Reversal of diet-induced hepatic steatosis and hepatic insulin resistance by antisense oligonucleotide inhibitors of Acetyl-CoA carboxylases 1 and 2" JCI Journal of Clinical Investigation, Mar. 2006 116(3)817-24.
H. James Harwood, Jr., et al.: "Enzyme Catalysis and Regulation: Oxidation in Cultured Cells and in Acid Synthesis, and Increase Fatty Acid Malonyl-CoA Concentrations, Inhibit Fatty Carboxylase Inhibitors Reduce Tissue Bipiperidylcarboxamide Acetyl-CoA Isozyme-nonselective N-Substituted Experimental Animals" Journal of Biological Chemistry Sep. 26, 2003, 278(39)37099-111.
"Reversal of Insulin Resistance in Rat Muscle by the Acetyl-CoA Carboxylase Inhibitor CP-640186" American Diabetes Association 2006 55 A288.
"The ACC Inhibitor CP-640186 Acutely Increases Muscle Fatty Acid Clearance Independently of Glucose Clearance and Cellular Energy Demand" American Diabetes Association 2006 55 A333.
L.Tong; "Acetyl-coenzyme A carboxylase: crucial metabolic enzyme and attractive target for drug discovery" CMLS, Cell. Mol. Life Sci. 62 (2005) 1784-1803.
L Makowsk, et al.: "Role of LKB1 in lung cancer development" British Journal of Cancer (2008) 99, pp. 683-688.
Chun Wang, et al.: "Acetyl-CoA carboxylase-a inhibitor TOFA induces human cancer cell apoptosis"; Biochemical and Biophysical Research Communications 385 (2009) 302-306.
Veronique Chaje, et al.: "Acetyl-CoA Carboxylase A Is Essential to Breast Cancer Cell Survival" Cancer Research May 15, 2006 vol. 66(10) pp. 5287-5294.

(Continued)

*Primary Examiner* — Jeffrey S Lundgren
*Assistant Examiner* — Michael J Schmitt
(74) *Attorney, Agent, or Firm* — Adam Warwick Bell; Matthew Rupert Kaser

(57) ABSTRACT

The present invention provides a compound suitable for use as an acetyl CoA carboxylase (ACC) inhibitor, specifically, a thienopyridine derivative, and use of the compound in the preparation of drugs for treating metabolic disorders, cancers or other proliferative disorders, and nonalcoholic steatohepatitis (NASH).

13 Claims, No Drawings

(56) References Cited

OTHER PUBLICATIONS

Annelies Beckers, Sophie Organe, Leen Timmermans, et al.; "Chemical Inhibition of Acetyl-CoA Carboxylase Induces Growth Arrest and Cytotoxicity Selectively in Cancer Cells" Cancer Research Sep. 1, 2007 vol. 67, pp. 8180-8187.
Koen Brusselmans, Ellen De Schrijver, Guido Verhoeven, et al.: "RNA Interference—Mediated Silencing of the Acetyl-CoA-Carboxylase-a Gene Induces Growth Inhibition and Apoptosis of Prostate Cancer Cells" Cancer Research 2005; 65: (15). Aug. 1, 2005, pp. 6719-6725.
Joan Brunet, et al.:"BRCA1 and Acetyl-CoA Carboxylase: The Metabolic Syndrome of Breast Cancer" Molecular Carcinogenesis 47:pp. 157-163 (2008).
Rob A. Cairns, et al,: "Regulation of cancer cell metabolism" Nature Reviews Cancer, Feb. 2011 vol. 11, pp. 85-95.
F. Chiaradonna, et al.: "From cancer metabolism to new biomarkers and drug targets" Biotechnology Advances, Jan.-Feb. 2012, pp. 30-51.
Carlotta Petti, et al.: "AMPK activators inhibit the proliferation of human melanomas bearing the activated MAPK pathway" Melanoma Research, Oct. 2012(5), 22: pp. 341-350.
Joan Brunet, et al.; "BRCA1 and Acetyl-CoA Carboxylase: The Metabolic Syndrome of Breast Cancer" Molecular Carcinogenesis (2008) 47(2): pp. 157-163.
Arne M. Olsen, et al.; "Fatty acid synthesis is a therapeutic target in human liposarcoma" International Journal of Oncology (2010) 36: pp. 1309-1314.

\* cited by examiner

ACC INHIBITOR AND USE THEREOF

TECHNICAL FIELD

The present invention belongs to the field of organic chemistry, and in particular, relates to an ACC inhibitor and use thereof.

BACKGROUND ART

Obesity is a health crisis for a large group of people. The health burden of obesity, measured by quality-adjusted life-years lost per adult, has surpassed that of smoking to become the most serious preventable cause of death. In the United States, about 34% of adults suffer from obesity, up from 31% in 1999 and about 15% in the years 1960 through 1980. Obesity increases the rate of mortality from all causes for both men and women at all ages and in all racial and ethnic groups. Obesity also leads to social stigmatization and discrimination, which decreases the quality of life dramatically. The chronic diseases that result from obesity cost the US economy more than 150 billion dollars in weight-related medical bills each year. In addition, about half of the obese population and 25% of the general population have metabolic syndrome, a disorder associated with abdominal obesity, hypertension, increased plasma triglycerides, decreased HDL cholesterol, and insulin resistance, which increases the risk for type-2 diabetes (T2DM), stroke and coronary heart disease. (Harwood, Expert Opin. Ther. Targets 9:267, 2005).

Diet and exercise, even when used in combination with the current pharmacotherapy, do not provide sustainable weight loss required for long-term health benefits. At present, only a few anti-obesity drugs are approved in the United States, including the fat absorption inhibitor orlistat, the 5-HT2C antagonist lorcaserin, and the combination therapy of phentermine/topiramate. Unfortunately, poor efficacy and adverse gastrointestinal side effects limits the use of orlistat. Surgery can be effective, but is limited to patients with extremely high body-mass indices (BMI). Moreover, the low throughput of surgery restricts the impact of this approach to about 200,000 patients per year. The majority of obesity drugs (for example, anorectics and satiety agents) in clinical development are designed to reduce caloric intake via a central action in the central nervous system (CNS). However, Food and Drug Administration (FDA) has taken an objection against CNS-active agents due to their modest efficacy and observed/potential side-effect profiles.

The continuing and increasing problem of obesity and the current lack of safe and effective drugs for treating obesity highlight the urgent need for a new drug to treat this disorder and its underlying cause.

In addition, non-alcoholic fatty liver disease (NAFLD) is a silent disease defined as a clinical pathological syndrome, which is mainly characterized by excessive fat deposition in liver cells caused by factors other than alcohol (alcohol consumption less than 20 g/day). NAFLD ranges from benign simple fatty liver (SFL) to non-alcoholic steatohepatitis (NASH) and cirrhosis associated therewith. Specifically, the accumulation of lipid droplets (LD) in the cytoplasm of more than 5% of liver cells in the normal liver is defined as hepatic steatosis, i.e., SFL; with the further development of hepatic steatosis, lobular inflammation, cell damage, etc. would occur to liver tissues, and then steatohepatitis, i.e., NASH, would be developed; and when steatohepatitis continuously aggravates, stellate cells are activated, and collagen fibers are deposited in the liver to lead to liver fibrosis, which continuously aggravates to result in liver cirrhosis. A necrosis/inflammatory process would accelerate the gradual accumulation of fibrosis in the liver, and eventually lead to liver failure, hepatocellular carcinoma (HCC), liver transplantation and liver death in addition to cirrhosis. From the perspectives of epidemiology and pathophysiology, NAFLD, in particular NASH, is closely related to metabolic disorders, such as obesity, insulin resistance, metabolic syndrome, and Type 2 diabetes. Over the past few decades, with the global prevalent trend of obesity and metabolic syndrome associated therewith, the prevalence of NAFLD, in particular NASH, has increased sharply. In particular, NASH has become an important cause of chronic liver disease in developed countries in Europe and the United States and in rich regions in China; and NASH has become the leading cause of liver transplantation in the United States. NASH represents an important stage during the development from SFL to liver fibrosis and liver cirrhosis. It is mainly characterized by hepatocyte steatosis, inflammatory cell infiltration and hepatic lobular fibrosis. NASH is considered to be an increasingly serious public health problem across the world. However, the current therapeutic protocol for NASH around the world is only limited to changing daily lifestyles, and there is no optimal diagnostic solution and approved therapeutic approach for NASH. Discovering and exploiting effective therapeutic drugs for NAFLD is one of the effective methods for preventing and treating NAFLD, in particular NASH, and it is also a scientific problem that needs to be solved urgently.

Another persistent problem is the lack of an antifungal drug that is active against a broad spectrum of fungal pathogens. Generally, a given antifungal drug shows activity against one fungal species, but lacks activity against other (and even closely related) specifies, such as *Candida albicans, Candida krusei*, and *Candida parapsilosis*.

A compound of Gilead can be effectively used as an inhibitor of acetyl-CoA carboxylase (ACC), and is suitable for the treatment of various diseases, disorders or conditions related to the regulation of fatty acid production or oxidation. Patent WO2019015583A1A discloses a compound of the following general formula:

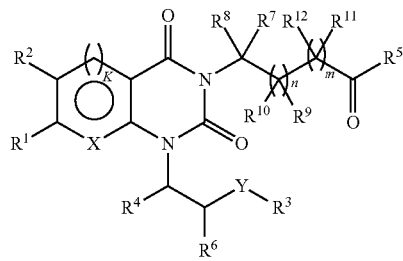

A compound of the present invention has the same parent nucleus structure as the above structure, with a difference in the terminal substitution of an N atom on a pyridine ring. The resulting compound can have a good inhibitory effect on ACC1 and ACC2, and a good inhibitory effect on HepG2 cells, showing excellent pharmacokinetic properties. The compound of the present invention and the pharmaceutically acceptable composition thereof can be used to treat a variety of diseases, disorders or conditions related to the regulation of fatty acid production or oxidation. In particular in the treatment of NAFLD, the compound of the present invention and the pharmaceutically acceptable composition thereof have a broad therapeutic prospect for a plurality of NAFLD stages from SFL to NASH and liver cirrhosis associated therewith, particularly NASH.

SUMMARY OF THE INVENTION

A compound of formula c

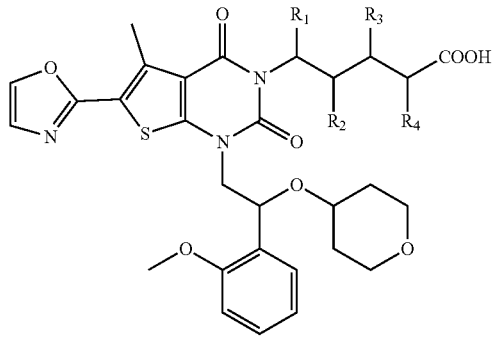

or a pharmaceutically acceptable salt thereof, wherein
$R_1$ is H, $C_{1-6}$ is alkyl, $C_{1-6}$ haloalkyl, or $C_{1-6}$ alkoxy;
$R_2$ is H, $C_{1-6}$ is alkyl, $C_{1-6}$ haloalkyl, or $C_{1-6}$ alkoxy;
$R_3$ is H, $C_{1-6}$ alkyl, $C_{1-6}$ haloalkyl, or $C_{1-6}$ alkoxy, or $R_1$ and $R_3$, together with a carbon atom bonded thereto, form 3-6 membered cycloalkyl; and
$R_4$ is H, $C_{1-6}$ alkyl, $C_{1-6}$ haloalkyl, or $C_{1-6}$ alkoxy, or $R_4$ and $R_2$, together with a carbon atom bonded thereto, form 3-6 membered cycloalkyl.

In some embodiments, $R_2$ and $R_4$ are each independently H, and $R_1$ and $R_3$ form a four-membered ring.

In some embodiments, $R_1$ and $R_3$ are each independently H, and $R_2$ and $R_4$ form a four-membered ring.

In some embodiments, the compound is:
(R)-3-((1-(2-(2-methoxyphenyl)-2-((tetrahydro-2H-pyran-4-yl)oxy)ethyl)-5-methyl-6-(oxazol-2-yl)-2,4-dioxa-1,4-dihydrothieno[2,3-d]pyrimidine-3(2H)-yl)methyl)cyclobutane-1-carboxylic acid;
(S)-3-((1-(2-(2-methoxyphenyl)-2-((tetrahydro-2H-pyran-4-yl)oxy)ethyl)-5-methyl-6-(oxazol-2-yl)-2,4-dioxa-1,4-dihydrothieno[2,3-d]pyrimidine-3(2H)-yl)methyl)cyclobutane-1-carboxylic acid;
(R)-2-(3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidine-3(2H)-yl)cyclobutyl)acetic acid;
(S)-2-(3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidine-3(2H)-yl)cyclobutyl)acetic acid;
2-((1R,3r)-3-(1-((R)-2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidine-3(4H)-yl)cyclobutyl)acetic acid; or
2-((1S,3s)-3-(1-((R)-2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidine-3(4H)-yl)cyclobutyl)acetic acid.

In some embodiments, a compound of formula I-3 is added to a compound of formula e or f for reaction to obtain a compound of formula I-4; or a compound of formula II-3 is added to the compound of formula e or f for reaction to obtain a compound of formula II-4; or a compound of formula I-3-1 is added to the compound of formula e or f for reaction to obtain a compound of formula I-4-1; or a compound of formula I-3-2 is added to the compound of formula e or f for reaction to obtain a compound of formula I-4-2. Preferably, the compound of formula e is 2-(triisopropylsilyl)oxazole, or 2-(tributylsilyl)oxazole; and the compound of formula f is 2-(triisopropylstannyl)oxazole, or 2-(tributylstannyl)oxazole. The specific structure of the compound can be found in the description below.

A compound of formula c' can be prepared from the compound of formula c.

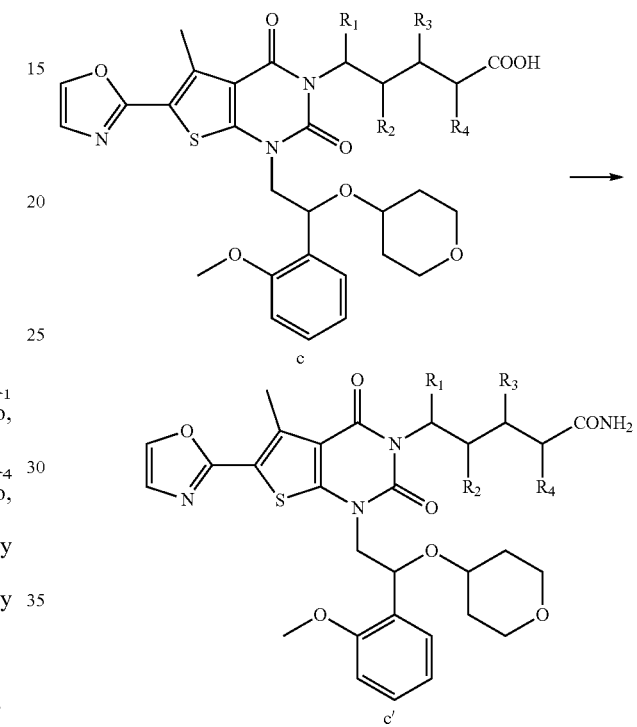

In some embodiments, the compound is:
(R)-3-((1-(2-(2-methoxyphenyl)-2-((tetrahydro-2H-pyran-4-yl)oxy)ethyl)-5-methyl-6-(oxazol-2-yl)-2,4-dioxa-1,4-dihydrothieno[2,3-d]pyrimidine-3(2H)-yl)methyl)cyclobutane-1-carboxamide;
(S)-3-((1-(2-(2-methoxyphenyl)-2-((tetrahydro-2H-pyran-4-yl)oxy)ethyl)-5-methyl-6-(oxazol-2-yl)-2,4-dioxa-1,4-dihydrothieno[2,3-d]pyrimidine-3(2H)-yl)methyl)cyclobutane-1-carboxamide;
(R)-2-(3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidine-3(2H)-yl)cyclobutyl)acetamide; or
(S)-2-(3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidine-3(2H)-yl)cyclobutyl)acetamide.

There is provided use of the compound defined above in preparing a drug for treating a metabolic disease. The metabolic disease is obesity, dyslipidemia or hyperlipidemia.

There is provided use of the compound defined above in preparing a drug for treating a cancer or other proliferative disorders.

The compound defined above is useful in preparing a drug for treating NAFLD in a plurality of stages from SFL to NASH and the liver cirrhosis associated therewith, in particular for treating non-alcoholic steatohepatitis (NASH).

As used herein, the term "pharmaceutically acceptable salt" refers to those salts which are, within the scope of sound medical judgment, suitable for use in contact with the tissues of humans and lower animals without undue toxicity, irritation, allergic response and other similar responses, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, which is incorporated herein by reference. Pharmaceutically acceptable salts of the compound of the present invention include those derived from suitable inorganic and organic acids and bases. Examples of pharmaceutically acceptable nontoxic acid addition salts are salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid, or by using other methods (such as ion exchange) used in the art. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline-earth metal salts include sodium, lithium, potassium, calcium, magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure, for example, the R and S configurations for each asymmetric center, Z and E double bond isomers, and Z and E conformational isomers. Therefore, single stereochemical isomers as well as enantiomeric, diastereomeric, and geometric (or conformational) mixtures of the compound of the present invention are within the scope of the present invention. Unless otherwise stated, all tautomeric forms of the compound of the present invention are within the scope of the present invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of the present invention. Such compounds are useful, for example, as analytical tools, as probes in biological assays, or as therapeutic agents in accordance with the present invention.

Use, Formulation and Administration and Pharmaceutically Acceptable Composition

According to another embodiment, the present invention provides a composition including a compound of the present invention or a pharmaceutically acceptable salt, ester, or ester-salt thereof and a pharmaceutically acceptable carrier, adjuvant, or vehicle. The amount of compound in the composition of the present invention is such that is effective to measurably inhibit ACC, in a biological sample or in a patient. In certain embodiments, the amount of compound in the composition of the present invention is such that is effective to measurably inhibit ACC, in a biological sample or in a patient. In certain embodiments, the composition of the present invention is formulated for administration to a patient in need of the composition. In some embodiments, the composition of the present invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the composition of the present invention include, but are not limited to, ion exchangers; alumina; aluminum stearate; lecithin; serum proteins, such as human serum albumin; buffer substances, such as phosphates; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyethylene glycol; sodium carboxymethylcellulose; polyacrylates; waxes; polyethylene-polyoxypropylene-block polymers; and polyethylene glycol and wool fat.

A "pharmaceutically acceptable derivative" means any non-toxic salt, ester, ester-salt or other derivatives of the compound of the present invention that, upon administration to a recipient, is capable of providing, either directly or indirectly, the compound of the present invention or an inhibitorily active metabolite or residue thereof.

As used herein, the term "inhibitorily active metabolite or residue thereof" means that a metabolite or residue thereof is also an ACC inhibitor.

The composition of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the composition is administered orally, intraperitoneally or intravenously. Sterile injectable forms of the composition of the present invention may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile fixed oil is conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated forms. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants (such as Tweens and Spans) and other emulsifying agents or bioavailability enhancers which are commonly used in the manufacture of pharmaceutically acceptable solid, liquid, or other dosage forms may also be used for the purposes of formulation.

The pharmaceutically acceptable composition of the present invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutically acceptable composition of the present invention may be administered in the form of suppositories for rectal administration. These suppositories can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable composition of the present invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the provided pharmaceutically acceptable composition may be formulated in a suitable ointment containing the active component suspended or dissolved in one or more carriers. Carriers for topical administration of compounds of the present invention include, but are not limited to, mineral oil, liquid petrolatum, white petrolatum, propylene glycol, polyoxyethylene, polyoxypropylene compound, emulsifying wax and water. Alternatively, the provided pharmaceutically acceptable composition can be formulated in a suitable lotion or cream containing the active components suspended or dissolved in one or more pharmaceutically acceptable carriers. Suitable carriers include, but are not limited to, mineral oil, Dehydrated sorbitol monostearate, polysorbate 60, cetyl esters wax, cetearyl alcohol, 2-octyldodecanol, benzyl alcohol and water.

For ophthalmic use, the provided pharmaceutically acceptable composition may be formulated as a micronized suspension in isotonic pH-adjusted sterile saline, or, preferably, as a solution in isotonic pH-adjusted sterile saline, either with or without a preservative such as benzylalkonium chloride. Alternatively, for ophthalmic uses, the pharmaceutically acceptable composition may be formulated in an ointment such as petrolatum.

The pharmaceutically acceptable composition of the present invention may also be administered by nasal aerosol or inhalation. Such composition is prepared according to techniques well-known in the art of pharmaceutical formulation and may be prepared as a solution in saline, employing benzyl alcohol or other suitable preservatives, absorption promoters to enhance bioavailability, fluorocarbons, and/or other conventional solubilizing or dispersing agents.

Most preferably, the pharmaceutically acceptable composition of the present invention is formulated for oral administration. Such formulation may be administered with or without food. In some embodiments, the pharmaceutically acceptable composition of the present invention is administered without food. In other embodiments, the pharmaceutically acceptable composition of the present invention is administered with food.

The amount of compounds of the present invention that may be combined with the carrier materials to produce a composition in a single dosage form will vary depending upon the host treated and the particular mode of administration.

Preferably, the provided compositions should be formulated such that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, age, body weight, general health, sex, diet, time of administration, rate of excretion, drug combination, and the judgment of the treating physician as well as the severity of the particular disease being treated. The amount of the compound of the present invention in the composition will also depend upon the particular compound in the composition.

Uses of Compound and Composition Thereof

Medical Uses

Acetyl-CoA carboxylase (ACC) catalyzes the ATP-dependent carboxylation of acetyl-CoA to form malonyl-CoA. This reaction, which proceeds in two half-reactions, a biotin carboxylase (BC) reaction and a carboxyltransferase (CT) reaction, is the first key step in fatty acid (FA) biosynthesis and is the rate-limiting reaction for the pathway. In addition to its role as a substrate in FA biosynthesis, malonyl-CoA, the product of the ACC-catalyzed reaction, also plays an important regulatory role in controlling mitochondrial FA uptake through allosteric inhibition of carnitine palmitoyltransferase I (CPT-I), the enzyme catalyzing the first committed step in mitochondrial FA oxidation. Malonyl-CoA, therefore, is a key metabolic signal for the control of FA production and utilization in response to dietary changes and altered nutritional requirements in animals, for example during exercise, and therefore plays a key role in controlling the switch between carbohydrate and fat utilization in the liver and skeletal muscle (Harwood, 2005).

In mammals, ACC exists as two tissue-specific isozymes, ACC1 which is present in lipogenic tissues (liver, adipose) and ACC2, which is present in oxidative tissues (liver, heart, skeletal muscle). ACC1 and ACC2 are encoded by separate genes, display distinct cellular distributions, and share 75% overall amino acid sequence identity, except for an extension at the N-terminus of ACC2 that direct ACC2 to the mitochondrial membrane. ACC1, which lacks this targeting sequence, is localized to the cytoplasm. In the heart and skeletal muscle, which have a limited capacity to synthesize fatty acids, the malonyl-CoA formed by ACC2 functions to regulate FA oxidation. In the liver, the malonyl-CoA formed in the cytoplasm through the actions of ACC1 is utilized for FA synthesis and elongation leading to triglyceride formation and VLDL production, whereas the malonyl-CoA formed at the mitochondrial surface by ACC2 acts to regulate FA oxidation (Tong and Harwood, J. Cellular Biochem. 99: 1476, 2006). This compartmentalization of malonyl-CoA results from a combination of synthesis proximity (Abu-Elheiga et al., PNAS (USA) 102: 12011, 2005) and the rapid action of malonyl-CoA decarboxylase (Cheng et al., J. Med. Chem. 49:1517, 2006).

Simultaneous inhibition of the enzymatic activities of ACC1 and ACC2 offers the ability to inhibit de novo FA production in lipogenic tissues (e.g. liver & adipose) while at the same time stimulating FA oxidation in oxidative tissues (e.g. liver & skeletal muscle) and therefore offers an attractive modality for favorably affecting, in a concerted manner, a multitude of cardiovascular risk factors associated with obesity, diabetes, insulin resistance, and the metabolic syndrome.

Several lines of evidence strongly support the concept of direct inhibition of ACC activity as an important therapeutic target for treating obesity, diabetes, insulin resistance, and the metabolic syndrome.

Abu-Elheiga et al. (Proc. Natl. Acad. Sci. USA 100: 10207-10212, 2003) demonstrated that ACC2 knock-out mice exhibit reduced skeletal and cardiac muscle malonyl-CoA, increased muscle FA oxidation, reduced hepatic fat, reduced total body fat, elevated skeletal muscle uncoupling protein-3 (UCP3) which is indicative of increased energy expenditure, reduced body weight, reduced plasma free FAs, reduced plasma glucose, and reduced tissue glycogen, and are protected from diet-induced diabetes and obesity.

Savage et al. (J. Clin. Invest. 116: 817, 2006), using ACC1 and ACC2 antisense oligonucleotides, demonstrated stimulation of FA oxidation in isolated rat hepatocytes and in rats fed high-fat diets, and lowering of hepatic triglycerides, improvements in insulin sensitivity, reductions in hepatic glucose production, and increases in UCP1 mRNA in high fat-fed rats. These effects were greater when both ACC1 and ACC2 expressions were suppressed than when either ACC1 or ACC2 expression alone was suppressed.

Harwood et al. (J. Biol. Chem. 278: 37099, 2003) demonstrated that the isozyme-nonselective ACC inhibitor, CP-640186, which equally inhibits ACC1 and ACC2 ($IC_{50}$=about 60 nM) isolated from rat, mouse, monkey and human without inhibiting either pyruvate carboxylase or propionyl-CoA carboxylase, reduced FA synthesis, triglyceride synthesis and secretion in Hep-G2 cells without affecting cholesterol synthesis, and reduced apoB secretion without affecting apoA1 secretion. CP-640186 also stimulated FA oxidation in C2C12 cells and in rat muscle slices and increased CPT-I activity in Hep-G2 cells. In experimental animals, CP-640186 acutely reduced malonyl-CoA concentration in both lipogenic and oxidative tissues in both the fed and fasted state, reduced liver and adipose tissue FA synthesis, and increased whole body FA oxidation. In sucrose-fed rats treated with CP-640186 for three weeks, CP-640186 time- and dose-dependently reduced liver, muscle and adipose triglycerides, reduced body weight due to selective fat reduction without reducing lean body mass, reduced leptin levels, reduced the hyperinsulinemia produced by the high sucrose diet without changing plasma glucose levels, and improved insulin sensitivity.

Saha et al. (Diabetes 55:A288, 2006) demonstrated stimulation of insulin sensitivity in insulin-resistant rat muscle tissue by CP-640186 within 30 min of compound administration, and studies by Furler et al. (Diabetes 55:A333, 2006) used dual tracer analysis to show that acute (46 min) treatment of rats with CP-640186 stimulated FA clearance without decreasing glucose clearance.

ACC is the rate-limiting enzyme in fatty acid synthesis and its product, malonyl CoA, serves as an important regulator of fatty acid oxidation. Hence, the ACC inhibitor both reduces de novo lipid synthesis and promotes the oxidation of existing fat. This dual effect on lipid metabolism raises the possibility that ACC inhibitors will be substantially more effective in reducing excess fat than other mechanisms. Furthermore, the ACC inhibitor will impact insulin sensitivity, plasma and tissue triglycerides, and fasting plasma glucose as a consequence of whole-body and tissue-specific fat mass reduction without the need for poly-pharmacy.

The ACC inhibitor need only access the liver and muscle in the peripheral compartment. Avoiding the CNS will address many of side effects associated with the late-stage obesity programs targeting CNS receptors. The ACC inhibitor is also expected to have a superior safety profile to existing metabolic disease agents. For instance, it is unlikely that an ACC inhibitor will precipitate life-threatening hypoglycemia as is often seen with insulin mimetics, insulin secretagogues, and insulin degradation inhibitors. Also, since the ACC inhibitor will reduce whole-body fat mass, it will be superior to the glitazone that increases whole-body fat mass as part of their mechanism of action.

A peripherally acting agent that causes significant weight loss and improves other metabolic endpoints fits well within the US FDA's requirements for approval of a new obesity agent. However, if an approval for obesity continues to be challenging in 5-7 years, the ACC inhibitor could be approved for familial combined hyperlipidemia and non-alcoholic steatohepatitis (NASH). There are currently no marketed ACC inhibitors, so an isozyme-nonselective ACC inhibitor would represent a first-in-class therapy for treating obesity and metabolic syndrome.

The activity of a compound utilized in the present invention as an inhibitor of ACC or treatment for obesity or metabolic syndrome, may be assayed in vitro or in vivo. An in vivo assessment of the efficacy of the compound of the present invention may be made using an animal model of obesity or metabolic syndrome, e.g., a rodent or primate model. Cell-based assays may be performed using, e.g., a cell line isolated from a tissue that expresses ACC. Additionally, biochemical or mechanism-based assays, e.g., transcription assays using a purified protein, RNA Northern blot, RT-PCR, etc., may be performed. In vitro assays include assays that determine cell morphology, protein expression, and/or the cytotoxicity, enzyme inhibitory activity, and/or the subsequent functional consequences of treatment of cells with the compound of the present invention. Alternate in vitro assays quantitate the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in the present invention as an inhibitor of ACC are set forth in the Examples below. The aforementioned assays are exemplary and not intended to limit the scope of the present invention. The skilled practitioner can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For instance, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compound and composition, according to the method of the present invention, may be administered using any amount and any route of administration effective for treating or lessening the severity of a metabolic disorder or condition, cancer, a bacterial infection, a fungal infection, a parasitic infection (e.g. malaria), an autoimmune disorder, a neurodegenerative or neurological disorder, schizophrenia, a bone-related disorder, a liver disease, or a cardiac disorder.

In some embodiments, the compound and composition, according to the method of the present invention, may be administered using any amount and any route of administration effective for treating or lessening the severity of a disease associated with ACC (Tong et al. "Acetyl-coenzyme A carboxylase:crucial metabolic enzyme and attractive target for drug discovery" Cell and Molecular Life Sciences (2005) 62, 1784-1803).

In some embodiments, the compound and composition, according to the method of the present invention, may be administered using any amount and any route of administration effective for treating or lessening the severity of a metabolic disorder, disease, or condition. In some embodiments, the metabolic disorder is obesity; metabolic syndrome; diabetes or diabetes-related disorders including Type 1 diabetes (insulin-dependent diabetes mellitus, IDDM) and Type 2 diabetes (non-insulin-dependent diabetes mellitus, NIDDM); impaired glucose tolerance; insulin resistance; hyperglycemia; diabetic complications, including, but not limited to atherosclerosis, coronary heart disease, stroke, peripheral vascular disease, nephropathy, hypertension, neuropathy and nephropathy; obesity comorbidities including but not limited to metabolic syndrome, dyslipidemia, hypertension, insulin resistance, diabetes (including Type 1 and Type 2 diabetes), coronary artery disease, and heart failure. In some embodiments, the metabolic disorder, disease, or condition is non-alcoholic fatty liver disease or hepatic insulin resistance.

In some embodiments, the present invention provides a method of treating a metabolic disorder, disease, or condition described herein, including administering a compound of the present invention in conjunction with one or more pharmaceutical agents. Suitable pharmaceutical agents that may be used in combination with the compound of the present invention include anti-obesity agents (including appetite suppressants), anti-diabetic agents, anti-hyperglycemic agents, lipid lowering agents, and anti-hypertensive agents.

Suitable lipid lowering agents that can be used in conjunction with the compound of the present invention include but are not limited to, bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR-alpha agonists, FXR receptor modulators, LXR receptor modulators, lipoprotein synthesis inhibitors, renin-angiotensin system inhibitors, PPAR-delta partial agonists, bile acid reabsorption inhibitors, PPAR-gamma agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin, and niacin-bound chromium.

Suitable anti-hypertensive agents that can be used in conjunction with the compound of the present invention include but are not limited to diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, alpha/beta adrenergic blockers, alpha 1 blockers, alpha 2 agonists, aldosterone inhibitors, mineralocorticoid receptor inhibitors, renin inhibitors, and angiopoietin 2 binding agents.

Suitable anti-diabetic agents that can be used in conjunction with the compound of the present invention include but are not limited to other acetyl-CoA carboxylase (ACC) inhibitors, DGAT-1 inhibitors, AZD7687, LCQ908, DGAT-2 inhibitors, monoacylglycerol O-acyltransferase inhibitors, PDE-10 inhibitors, AMPK activators, sulfonylureas (e.g. acetohexamide, chlorpropamide, diabinese, glibenclamide, glipizide, glyburide, blimipiride, gliclazide, glipentide, gliquidone, glisolamide, tolazamide, tolbutamide), meglitinides, alpha-amylase inhibitors (e.g. tendamistat, treastatin, AL-3688), alpha-glucoside hydrolase inhibitors (e.g. acarbose), alpha-glucosidase inhibitors (e.g. adiposine, camiglibose, emiglitate, miglitol, voglibose, pradimicin-Q, sarbostatin), PPAR-gamma agonists (e.g. balaglitazone, ciglitazone, darglitazone, englitazone, isaglitazone, pioglitazone, rosiglitazone, troglitazone), PPAR-alpha/gamma agonists (e.g. CLX-0940, GW-1536, GW-1929, GW-2433, KRP-297, L-796449, LR-90, MK-0767, SB-219994), biguanides (e.g. metformin, buformin), GLP-1 modulators (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitors (e.g. resveratrol, GSK2245840, GSK184072), DPP-IV inhibitors (e.g. sitagliptin, vildagliptin, alogliptin, dutogliptin, linagliptin, saxagliptin), insulin secretagogues, fatty acid oxidation inhibitors, A2 antagonists, JNK inhibitors, glucokinase activators (e.g. TTP-399, TTP-355, TTP-547, AZD1656, ARRY403, MK-0599, TAK-329, AZD5658, GKM-001), insulin, insulin mimetics, glycogen phosphorylase inhibitors (e.g. GSK1362885), VPAC2 receptor agonists, SGLT2 inhibitors (dapagliflozin, canagliflozin, BI-10733, tofogliflozin, ASP-1941, THR1474, TS-071, LX4211), glucagon receptor modulators, GPR119 modulators (e.g. MBX-2982, GSK1292263, APD597, PSN821), FGF21 derivatives, TGR5 (GPBAR1) receptor agonists (e.g. INT777), GPR40 agonists (e.g. TAK-875), GPR120 agonists, nicotinic acid receptor (HM74A) activators, SGLT1 inhibitors (e.g. GSK1614235), carnitine palmitoyl transferase enzyme inhibitors, fructose 1,6-diphosphatase inhibitors, aldose reductase inhibitors, mineralocorticoid receptor inhibitors, TORC2 inhibitors, CCR2 inhibitors, CCR5 inhibitors, PKC (e.g. PKC-alpha, PKC-beta, PKC-gamma) inhibitors, fatty acid synthetase inhibitors, serine palmitoyl transferase inhibitors, GPR81 modulators, GPR39 modulators, GPR43 modulators, GPR41 modulators, GPR105 modulators, Kv1.3 inhibitors, retinol binding protein 4 inhibitors, glucocorticoid receptor modulators, somatostatin receptor (e.g. SSTR1, SSTR2, SSTR3, SSTR5) inhibitors, PDHK2 inhibitors, PDHK4 inhibitors, MAP4K4 inhibitors, IL1-beta modulators, and RXR-alpha modulators.

Suitable anti-obesity agents include but are not limited to, 11-beta-hydroxysteroid dehydrogenase 1 inhibitors, stearoyl-CoA desaturase (SCD-1) inhibitors, MCR-4 agonists, CCK-A agonists, monoamine reuptake inhibitors (e.g. sibutramine), sympathomimetic agents, beta-3-adrenergic receptor agonists, dopamine receptor agonists (e.g. bromocriptine), melanocyte-stimulating hormone and analogs thereof, 5-$HT_{2C}$ agonists (e.g. lorcaserin/Belviq), melanin concentrating hormone antagonists, leptin, leptin analogs, leptin agonists, galanin antagonists, lipase inhibitors (e.g. tetrahydrolipstatin/Orlistat), anorectic agents (e.g. bombesin agonists), NPY antagonists (e.g. velneperit), $PYY_{3-36}$ (and analogs thereof), BRS3 modulators, opioid receptor mixed antagonists, thyromimetic agents, dehydroepiandrosterone, glucocorticoid agonists or antagonists, orexin antagonists, GLP-1 agonists, ciliary neurotrophic factors (e.g. Axokine), human agouti-related protein (AGRP) inhibitors, H3 antagonists or inverse agonists, neuromedin U agonists, MTP/ApoB inhibitors (e.g. gut-selective MTP inhibitors such as dirlotapide, JTT130, Usistapide, SLX4090), MetAp2 inhibitors (e.g. ZGN-433), agents with mixed modulatory activity at two or more of glucagon, GIP, and GLP1 receptors (e.g. MAR-701, ZP2929), norepinephrine reuptake inhibitors, opioid antagonists (e.g. naltrexone), CB1 receptor antagonists or inverse agonists, ghrelin agonists or antagonists, oxyntomodulin and analogs thereof, monoamine uptake inhibitors (e.g. tesofensine), and combination agents (e.g. buproprion plus zonisamide (Empatic), pramlintide plus metreleptin, buproprion plus naltrexone (Contrave), phentermine plus topiramate (Qsymia).

In some embodiments, the anti-obesity agents used in combination with the compound of the present invention are selected from gut-selective MTP inhibitors (e.g. dirlotapide, mitratapide, implitapide, R56918), CCK-A agonists, 5-HT2c agonists (e.g. lorcaserin/Belviq), MCR4 agonists, lipase inhibitors (e.g. Cetilistat), $PYY_{3-36}$ (including analogs and PEGylated analogs thereof), opioid antagonists (e.g. naltrexone), oleoyl estrone, obinepitide, pramlintide, tesofensine, leptin, bromocriptine, orlistat, AOD-9604, and sibutramine.

In some embodiments, the compound and composition, according to the method of the present invention, may be administered using any amount and any route of administration effective for treating or lessening the severity of a LKB1 or Kras associated disease. In some embodiments, the LKB1 or Kras associated disease is selected from hepatocellular carcinoma, LKB1 mutant cancers, LKB1 loss of heterozygosity (LOH) driven cancers, Kras mutant cancers, Peutz-Jeghers syndrome (PJS), Cowden's disease (CD), and tubeous sclerosis (TS) (Makowski et al. "Role of LKB1 in Lung Cancer Development" British Journal of Cancer (2008) 99, 683-688). In some embodiments, the LKB1 or Kras associated disease is a Kras positive/LKB1 deficient lung tumor.

In some embodiments, the compound and composition, according to the method of the present invention, may be administered using any amount and any route of administration effective for treating or lessening the severity of a cancer, or inhibiting the growth of or inducing apoptosis in cancer cells (Wang et al. "Acetyl-CoA Carboxylase-alpha Inhibitor TOFA Induces Human Cancer Cell Apoptosis" BiochemBiophys Res Commun. (2009) 385(3), 302-306; Chajes et al. "Acetyl-CoA Carboxylase alpha Is Essential to Breast Cancer Cell Survival" Cancer Res. (2006) 66, 5287-5294; Beckers et al. "Chemical Inhibition of Acetyl-CoA Carboxylase Induces Growth Arrest and Cytotoxicity Selectivity in Cancer Cells" Cancer Res. (2007) 8180-8187; Brusselmans et al. "RNA Interference-Mediated Silencing of the Acetyl-CoA-Carboxylase-alpha Gene Induces Growth Inhibition and Apoptosis of Prostate Cancer Cells" Cancer Res. (2005) 65, 6719-6725; Brunet et al. "BRCA1 and Acetyl-CoA Carboxylase: The Metabolic Syndrom of Breast Cancer" Molecular Carcinogenesis (2008) 47, 157-163; Cairns et al. "Regulation of Cancer Cell Metabolism" (2011) 11, 85-95; Chiaradonna et al. "From Cancer Metabolism to New Biomarkers and Drug Targets" Biotechnology Advances (2012) 30, 30-51).

In some embodiments, the compound and composition, according to the method of the present invention, may be administered using any amount and any route of administration effective for treating or lessening the severity of NAFLD. In some embodiments, NAFLD is SFL, NASH and liver cirrhosis associated therewith, preferably NASH.

In some embodiments, the compound and composition, according to the method of the present invention, may be administered using any amount and any route of administration effective for treating or lessening the severity of melanoma. In some embodiments, the melanoma is one bearing an activated MAPK pathway (Petti et al. "AMPK activators inhibit the proliferation of human melanomas bearing the activated MAPK pathway" Melanoma Research (2012) 22, 341-350).

The compound of the present invention finds special utility in triple negative breast cancer, as the tumor suppressor protein BRCA1 binds and stabilizes the inactive form of ACC, thus upregulating de novo lipid synthesis, resulting in cancer cell proliferation (Brunet et al. "BRCA1 and acetyl-CoA carboxylase: the metabolic syndrome of breast cancer" Mol. Carcinog. (2008) 47(2), 157-163).

In some embodiments, the compound and composition, according to the method of the present invention, may be administered using any amount and any route of administration effective for treating or lessening the severity of a liposarcoma. The liposarcoma have been shown to depend on de novo long-chain fatty acid synthesis for growth, and inhibition of ACC by soraphen A inhibited lipogenesis as well as tumor cell growth (Olsen et al. "Fatty acid synthesis is a therapeutic target in human liposarcoma" International J. of Oncology (2010) 36, 1309-1314).

In some embodiments, the compound and composition, according to the method of the present invention, may be administered using any amount and any route of administration effective for treating or lessening the severity of a liver disease. In some embodiments, the liver disease is selected from hepatitis C, hepatocellular carcinoma, familial combined hyperlipidemia and non-alcoholic steatohepatitis (NASH), liver cancer, cholangiocarcinoma, angiosarcoma, hemangiosarcoma, and progressive familial intrahepatic cholestasis.

The exact amount required will vary from subject to subject, depending on the species, age, and general condition of the subject, the severity of the infection, the particular agent, its mode of administration, and the like. The compound of the present invention is preferably formulated in dosage unit form for ease of administration and uniformity of dosage. The expression "dosage unit form" as used herein refers to a physically discrete unit of agent appropriate for the patient to be treated. It will be understood, however, that the total daily usage of the compound and composition of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The pharmaceutically acceptable composition of the present invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In a particular embodiment, the compound of the present invention may be administered orally or parenterally at a dosage level of about 0.01 mg/kg to about 50 mg/kg and preferably from about 1 mg/kg to about 25 mg/kg of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. The acceptable vehicles and solvents that may be employed include water, Ringer's solution, U.S.P. and isotonic sodium chloride solution. In addition, sterile fixed oils are conventionally employed as a solvent or suspending medium. For this purpose, any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of the compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers (such as polylactide-polyglycolide). Depending upon the ratio of compound to polymer and the nature of the particular polymer employed, the rate of compound release can be controlled. Examples of other biodegradable polymers include poly(orthoesters) and poly (anhydrides). Depot injectable formulations are also prepared by entrapping the compound in liposomes or microemulsions that are compatible with body tissues.

A composition for rectal or vaginal administration is preferably a suppository which can be prepared by mixing the compound of the present invention with suitable non-irritating excipients or carriers (such as cocoa butter and polyethylene glycol) or a suppository wax, which is solid at ambient temperature but liquid at body temperature and therefore melts in the rectum or vaginal cavity and releases the active compound.

Solid dosage forms for oral administration include capsules, tablets, pills, powders, and granules. Among such solid dosage forms, the active compound is mixed with at least one of the following inert pharmaceutically acceptable excipient or carriers: sodium citrate or dicalcium phosphate; and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also include buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells (such as enteric coatings and other coatings well known in the pharmaceutical formulating art). They may optionally contain opacifying agents, and can also be of a composition that they release the active ingredient only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also include, as is normal practice, additional substances other than inert diluents, e.g., tableting lubricants and other tableting aids such a magnesium stearate and microcrystalline cellulose. In the case of capsules, tablets and pills, the dosage forms may also include buffering agents. They may optionally contain opacifying agents and can also be of a composition that they release the active ingredient only, or preferentially, in a certain part of the intestinal tract, optionally, in a delayed manner. Examples of embedding compositions that can be used include polymeric substances and waxes.

Dosage forms for topical or transdermal administration of the compound of the present invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and eye drops are also contemplated as being within the scope of the present invention. Additionally, the present invention encompasses the use of transdermal patches, which have the added advantage of providing controlled delivery of a compound to the body. Such dosage forms can be made by dissolving or dispensing the compound in a proper medium. Absorption enhancers can also be used to increase the flux of the compound across the skin. The rate can be controlled by either providing a rate controlling membrane or by dispersing the compound in a polymer matrix or gel.

According to one embodiment, the present invention relates to a method for inhibiting ACC in a biological sample, including the step of contacting said biological sample with the compound of the present invention, or the composition containing said compound.

In a particular embodiment, the present invention relates to a method for modulating fatty acid levels in a biological sample, including the step of contacting said biological sample with the compound of the present invention, or the composition containing said compound.

The term "biological sample", as used herein, includes, but is not limited to, cell cultures or extracts thereof; biopsied material obtained from a mammal or extracts thereof; and blood, saliva, urine, feces, semen, tears, or other body fluids or extracts thereof. Inhibition of enzymes in a biological sample is useful for a variety of purposes that are known to a person skilled in the art. Examples of such purposes include, but are not limited to, biological assays, gene expression studies, and biological target identification.

Another embodiment of the present invention relates to a method for inhibiting ACC in a patient, including the step of administering to said patient the compound of the present invention, or the composition containing said compound.

According to another embodiment, the present invention relates to a method for inhibiting fatty acid production, stimulating fatty acid oxidation, or both, in a patient, including the step of administering to said patient the compound of the present invention, or the composition containing said compound. According to a particular embodiment, the present invention relates to a method for inhibiting fatty acid production, stimulating fatty acid oxidation, or both in a patient so as to decrease obesity or alleviate symptoms of metabolic syndrome, including the step of administering to said patient the compound of the present invention, or the composition containing said compound. In other embodiments, the present invention provides a method for treating a disorder mediated by ACC in a patient in need thereof, including the step of administering to said patient the compound according to the present invention or the pharmaceutically acceptable composition thereof. Such disorder is described in detail herein.

In some embodiments, the compound and composition of the present invention may be used in a method for treating obesity or another metabolic disorder. In a particular embodiment, the compound and composition of the present invention may be used to treat obesity or other metabolic disorder in a mammal. In a particular embodiment, the mammal is a human patient. In a particular embodiment, the compound and composition of the present invention may be used to treat obesity or other metabolic disorder in a human patient.

In some embodiments, the present invention provides a method for treating obesity or another metabolic disorder, including administering the compound or composition of the present invention to a patient with obesity or another metabolic disorder. In a particular embodiment, the method for treating obesity or another metabolic disorder includes administering the compound and composition of the present invention to a mammal. In a particular embodiment, the mammal is a human. In some embodiments, the metabolic disorder is dyslipidemia or hyperlipidemia. In some embodiments, the obesity is a symptom of Prader-Willi syndrome, Bardet-Biedl syndrome, Cohen syndrome or MOMO syndrome. In some embodiments, the obesity is a side effect resulting from the administration of another drug, which includes but is not limited to insulin, sulfonylureas, thiazolidinediones, antipsychotics, antidepressants, steroids, anticonvulsants (including phenytoin and valproate), pizotifen, or hormonal contraceptives.

In a particular embodiment, the present invention provides a method for treating cancer or another proliferative disorder, including administering the compound or composition of the present invention to a patient with cancer or another proliferative disorder. In a particular embodiment, the method for treating cancer or another proliferative disorder includes administering the compound and composition of the present invention to a mammal. In a particular embodiment, the mammal is a human.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells, whose proliferation is inhibited by the compound and composition described herein and against which the method described herein is useful, include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by the compound or composition of the present invention is a melanoma, liposarcoma, lung cancer, breast cancer, prostate cancer, leukemia, kidney cancer, esophageal cancer, brain cancer, lymphoma or colon cancer. In a particular embodiment, the cancer is a primary effusion lymphoma (PEL). In certain preferred embodiments, the cancer to be treated by the compound or composition of the present invention is one bearing an activated MAPK pathway. In some embodiments, the cancer bearing the activated MAPK pathway is a melanoma. In certain preferred embodiments, the cancer treated by the compound or composition of the present invention is one associated with BRCA1 mutation. In an especially preferred embodiment, the cancer treated by the compound or composition of the present invention is a triple negative breast cancer.

In a particular embodiment, the disease which can be treated by the compound of the present invention is a neurological disorder. In some embodiments, the neurological disorder is Alzheimer's disease, Parkinson's disease, epilepsy, ischemia, age associated memory impairment, mild cognitive impairment, Friedreich's ataxia, GLUT1-deficient epilepsy, leprechaunism, Rabson-Mendenhall syndrome, coronary arterial bypass graft dementia, anaesthesia-induced memory loss, amyotrophic lateral sclerosis, or gliomaor Huntington's Disease.

In a particular embodiment, a provided compound, or a composition thereof, is administered in combination with another ACC inhibitor or antiobesity agent. In some embodiments, a provided compound, or a composition thereof, is administered in combination with one or more other therapeutic agents. Such is therapeutic agents include, but are not limited to, agents such as orlistat (Xenical), CNS stimulants, Qsymia, or Belviq.

In a particular embodiment, a provided compound, or a composition thereof, is administered in combination with another anti-cancer, cytotoxin, or chemotherapeutic agent, to a patient in need thereof.

In a particular embodiment, the anti-cancer or chemotherapeutic agent used in combination with the compound or composition of the present invention includes, but is not limited to, metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-retinoic acid, 2-CdA, 2-chlorodeoxyadenosine, 5-azacitidine, 5-fluorouracil, 5-FU, 6-mercaptopurine, 6-MP, 6-TG, 6-thioguanine, abraxane, or combinations of any of the above.

In a particular embodiment, the compound of the present invention may be administered together with a biguanide selected from metformin, phenformin, or buformin, to a patient in need thereof. In a particular embodiment, the patient administered a combination of the compound of the present invention and a biguanide is suffering from a cancer, obesity, a liver disease, diabetes or two or more of the above.

In a particular embodiment, a combination of two or more therapeutic agents may be administered together with the compound of the present invention.

In certain embodiments, a combination of three or more therapeutic agents may be administered with the compound of the present invention.

Other examples of agents, with which the inhibitor of the present invention may also be combined, include, without limitation: vitamins and nutritional supplements; cancer vaccines; therapies for neutropenia (e.g. G-CSF, filgrastim, and lenograstim); therapies for thrombocytopenia (e.g. blood transfusion and erythropoietin); PI3 kinase (PI3K) inhibitors; MEK inhibitors; AMPK activators; PCSK9 inhibitors; SREBP site 1 protease inhibitors; HMG CoA-reductase inhibitors; antiemetics (e.g. 5-HT$_3$ receptor antagonists, dopamine antagonists, NK1 receptor antagonists, histamine receptor antagonists, cannabinoids, benzodiazepines); agents for treating schizophrenia such as zyprexa, risperdal, seroquel, and haloperidol; anti-inflammatory agents such as corticosteroids, TNF blockers, IL-IRA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and salazosulfapyridine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, and buformin), thiazolidinediones (rosiglitazone, pioglitazone, and troglitazone), sulfonylureas (tolbutamide, acetohexamide, tolazamide, chlorpropamide, glipizide, glyburide, glimepiride, and gliclazide), meglitinides (repaglinide and nateglinide), alpha-glucosidase inhibitors (miglitol and acarbose), incretin mimetics (exenatide, liraglutide, and taspoglutide), gastric inhibitory peptide analogs, DPP-4 inhibitors (vildagliptin, sitagliptin, saxagliptin, linagliptin, and alogliptin), amylin analogs (pramlintide), and insulin and insulin analogs.

In a particular embodiment, the compound of the present invention, or the pharmaceutically acceptable composition thereof, is administered in combination with antisense agents, a monoclonal or polyclonal antibody or an siRNA therapeutic agent.

Those additional agents may be administered separately from the compound or composition of the present invention, as part of a multiple dosage regimen. Alternatively, those agents may be part of a single dosage form, mixed together with the compound of the present invention in a single composition. If administered as part of a multiple dosage regime, two active agents may be provided simultaneously, sequentially or within a period of time from one another, normally within five hours from one another.

As used herein, the term "combination," "combined," and related terms refers to the simultaneous or sequential administration of therapeutic agents in accordance with the present invention. For instance, the compound of the present invention may be administered with another therapeutic agent simultaneously or sequentially in separate unit dosage forms or together in a single unit dosage form. Accordingly, the present invention provides a single unit dosage form including the compound of the present invention, an additional therapeutic agent, and a pharmaceutically acceptable carrier, adjuvant, or vehicle.

The amount of both, the compound of the present invention and the additional therapeutic agent (in those compositions which include the additional therapeutic agent as described above) that may be combined with the carrier materials to produce a single dosage form will vary depending upon the host treated and the particular mode of administration. Preferably, the composition of the present invention should be formulated such that a dosage of 0.01-100 mg/kg body weight/day of can be administered.

In those compositions which include an additional therapeutic agent, said additional therapeutic agent and the compound of the present invention may act synergistically. Therefore, the amount of the additional therapeutic agent in such composition would be less than that required in a monotherapy utilizing only that therapeutic agent. In these compositions, a dosage of 0.01-100 μg/kg body weight/day of the additional therapeutic agent can be administered.

The amount of the additional therapeutic agent present in the composition of the present invention would be no more than the amount that would normally be administered in a composition including that therapeutic agent as the only active agent. Preferably the amount of the additional therapeutic agent in the disclosed composition of the present invention would range from about 50% to 100% of the amount normally present in a composition including that agent as the only therapeutically active agent.

DETAILED DESCRIPTION OF THE PREFERRED EMBODIMENTS

The embodiments of the present invention will be described in more detail below in conjunction with the schematic diagrams. The advantages and features of the present invention would be clearer based on the following description. It should be noted that the accompanying drawings are provided at non-accurate scale in a very simple form only for the purpose of conveniently and clearly assisting the explanation of the examples of the present invention.

Synthesis of Intermediate (R)-4-(2-bromo-1-(2-methoxyphenyl)ethyoxyl)tetrahydro-2H-pyran 3.61

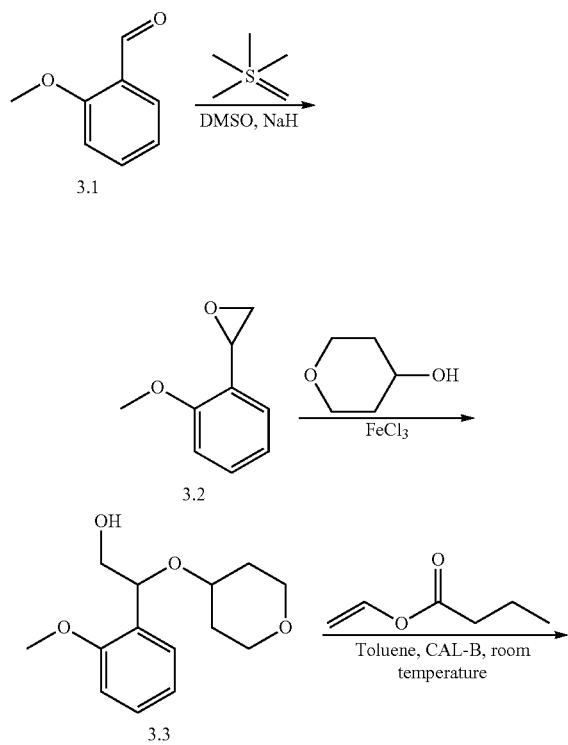

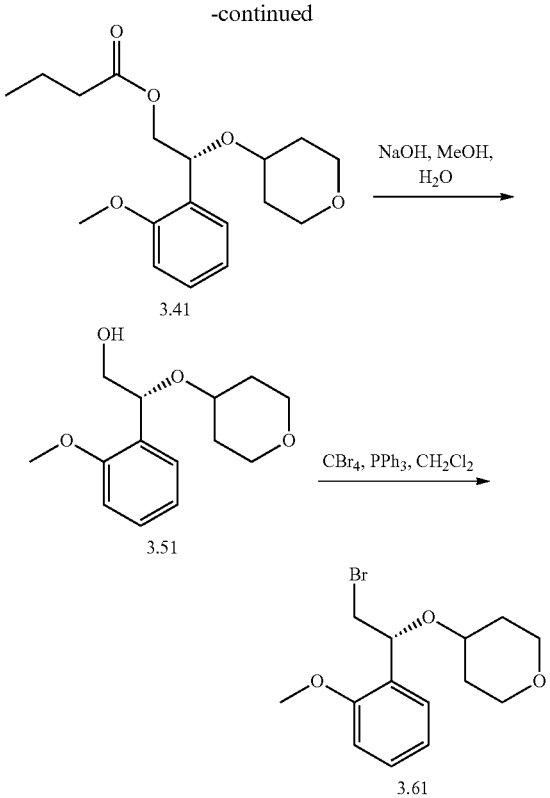

Method A
Method A:
Synthesis of Compound 3.2
In the presence of nitrogen, DMSO is put in to a round-bottom flask. Then NaH is added. The mixture is stirred at room temperature. At room temperature, trimethylsulfoxide iodide is added to the mixture in batches. A resulting solution is stirred. A compound 3.1 is dropwise added to the mixture, and a reaction mixture is stirred at room temperature, and then quenched by adding NH$_4$Cl (aqueous solution). A resulting solution is extracted with EtOAc; and organic layers are combined, dried with anhydrous Na$_2$SO$_4$ and concentrated in vacuum to obtain 3.2 as a yellow oil.

Synthesis of Compound 3.3
In the presence of nitrogen, tetrahydropyran-4-ol and FeCl$_3$ is added to a round-bottom flask. Then, 3.2 is dropwise added. A reaction mixture is stirred at room temperature. A resulting solution is diluted with H$_2$O, and then extracted with EtOAc. Organic layers are combined and a solvent is removed in vacuum. A crude product is purified by column chromatography to obtain 3.3 as a white solid.

Synthesis of Compound 3.41
3.3, toluene, CAL-B, and vinyl butyrate are added to a round-bottom flask. A reaction mixture is stirred at room temperature. Filtration is carried out to remove solids, and a filtrate is concentrated in vacuum to obtain 3.41 as a colorless oil.

Synthesis of Compound 3.51
3.41, methanol, water, and NaOH are added to a round-bottom flask. A reaction mixture is stirred at room temperature and then quenched by addition of acetic acid. A resulting mixture is concentrated in vacuum, and then extracted with EtOAc. Organic layers are combined and concentrated in vacuum. A crude product is purified by column chromatography to obtain 3.51 as a white solid.

Synthesis of Compound 3.61

In the presence of nitrogen, 3.51, CBr$_4$, CH$_2$Cl$_2$, and PPh$_3$ are added to a round-bottom flask. A reaction mixture is stirred at room temperature overnight and then concentrated in vacuum. A crude product is purified by column chromatography to obtain 3.61 as a yellow oil.

Synthesis of Intermediate (S)-4-(2-bromo-1-(2-methoxyphenyl)ethyoxyl)tetrahydro-2H-pyran 3.62

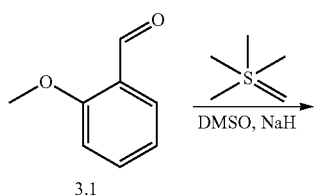
3.1

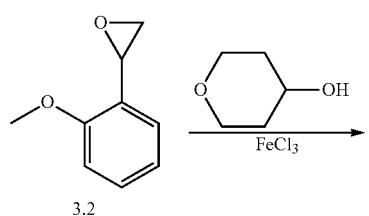
3.2

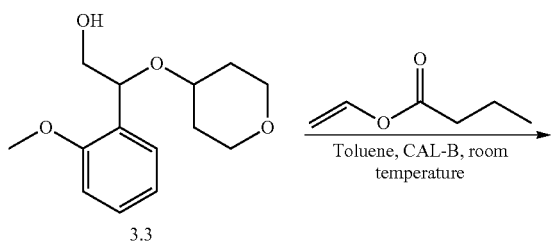
3.3

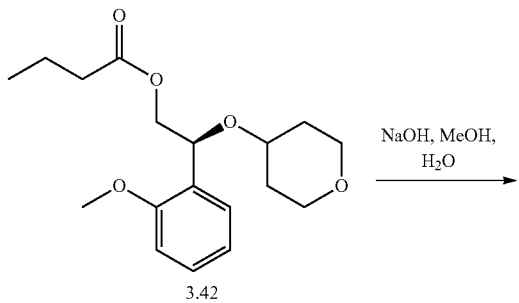
3.42

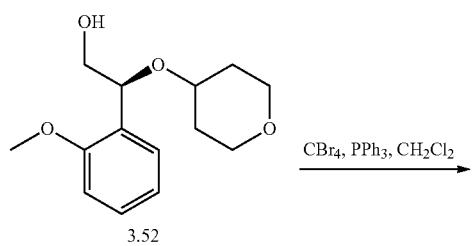
3.52

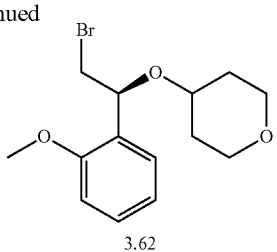
3.62

Method B
Method B:
Synthesis of Compound 3.2

In the presence of nitrogen, DMSO is put in to a round-bottom flask. Then NaH is added. The mixture is stirred at room temperature. At room temperature, trimethylsulfoxide iodide is added to the mixture in batches. A resulting solution is stirred. A compound 3.1 is dropwise added to the mixture, and a reaction mixture is stirred at room temperature, and then quenched by adding NH$_4$Cl (aqueous solution). A resulting solution is extracted with EtOAc; and organic layers are combined, dried with anhydrous Na$_2$SO$_4$ and concentrated in vacuum to obtain 3.2 as a yellow oil.

Synthesis of Compound 3.3

In the presence of nitrogen, tetrahydropyran-4-ol and FeCl$_3$ is added to a round-bottom flask. Then, 3.2 is dropwise added. A reaction mixture is stirred at room temperature. A resulting solution is diluted with H$_2$O, and then extracted with EtOAc. Organic layers are combined and a solvent is removed in vacuum. A crude product is purified by column chromatography to obtain 3.3 as a white solid.

Synthesis of Compound 3.42

3.3, toluene, CAL-B, and vinyl butyrate are added to a round-bottom flask. A reaction mixture is stirred at room temperature. Filtration is carried out to remove solids, and a filtrate is concentrated in vacuum to obtain 3.42 as a colorless oil.

Synthesis of Compound 3.52

3.42, methanol, water, and NaOH are added to a round-bottom flask. A reaction mixture is stirred at room temperature and then quenched by addition of acetic acid. A resulting mixture is concentrated in vacuum, and then extracted with EtOAc. Organic layers are combined and concentrated in vacuum. A crude product is purified by column chromatography to obtain 3.52 as a white solid.

Synthesis of Compound 3.62

In the presence of nitrogen, 3.52, CBr$_4$, CH$_2$Cl$_2$, and PPh$_3$ are added to a round-bottom flask. A reaction mixture is stirred at room temperature overnight and then concentrated in vacuum. A crude product is purified by column chromatography to obtain 3.62 as a yellow oil.

Synthesis of Compound of Formula e

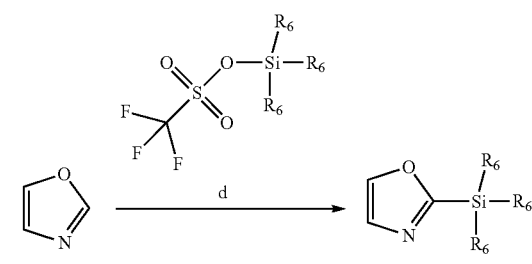
e

Method C
Method C:
Oxazole and a compound d are added to THF, stirred, dried, filtered and purified to obtain a compound of formula e. $R_6$ is $C_{3-6}$ alkyl.
Synthesis of Compound of Formula f
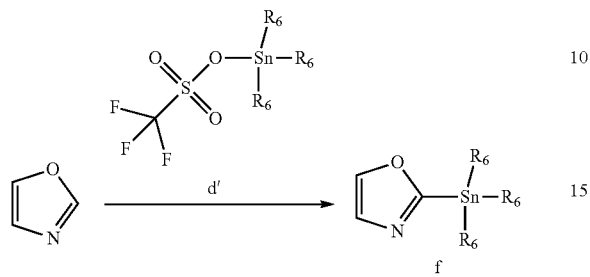
Method F
Method F:
Oxazole and a compound d' are added to THF, stirred, dried, filtered and purified to obtain a compound of formula f. $R_6$ is $C_{3-6}$ alkyl.
Synthesis of Compound of Formula c
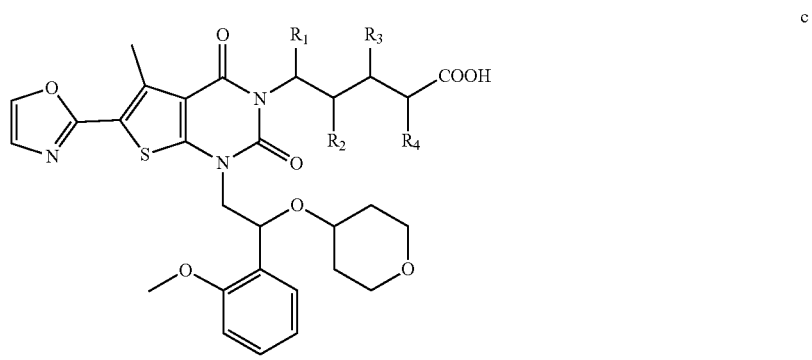
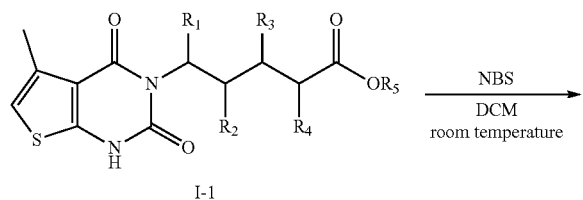
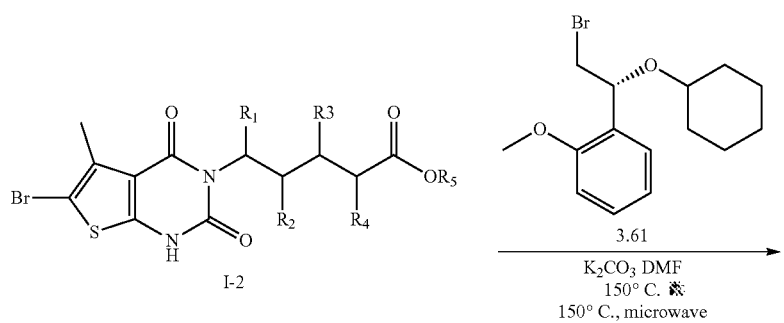

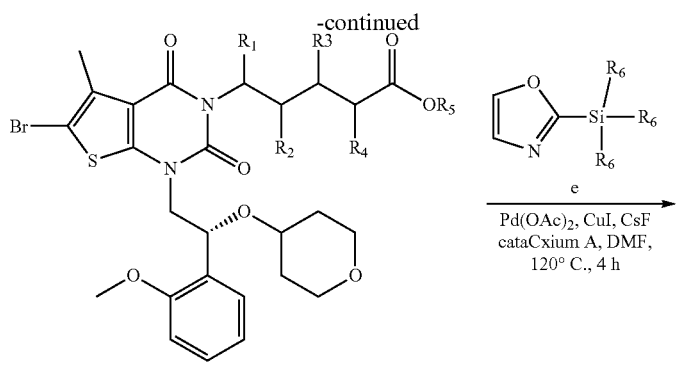

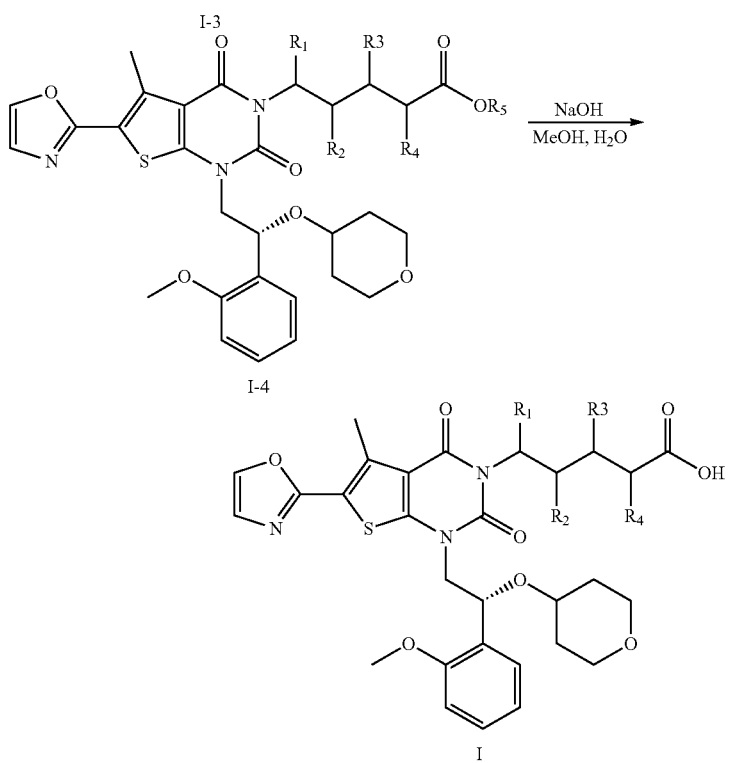

Method D:

An intermediate I-1 can be prepared by using a method known in the prior art, and further reaction is conducted according to method D to obtain a compound of general formula I. $R_1$ is H, $C_{1-6}$ alkyl, $C_{1-6}$ haloalkyl, or $C_{1-6}$ alkoxy; $R_2$ is H, $C_{1-6}$ alkyl, $C_{1-6}$ haloalkyl, or $C_{1-6}$ alkoxy; $R_3$ is H, $C_{1-6}$ alkyl, $C_{1-6}$ haloalkyl, or $C_{1-6}$ alkoxy, or $R_1$ and $R_3$, together with a carbon atom bonded thereto, form 3-6 membered cycloalkyl; and $R_4$ is H, $C_{1-6}$ alkyl, $C_{1-6}$ haloalkyl, or $C_{1-6}$ alkoxy, or $R_4$ and $R_2$, together with a carbon atom bonded thereto, form 3-6 membered cycloalkyl. $R_5$ is $C_{1-6}$ alkyl. $R_6$ is $C_{3-6}$ alkyl.

Method G:

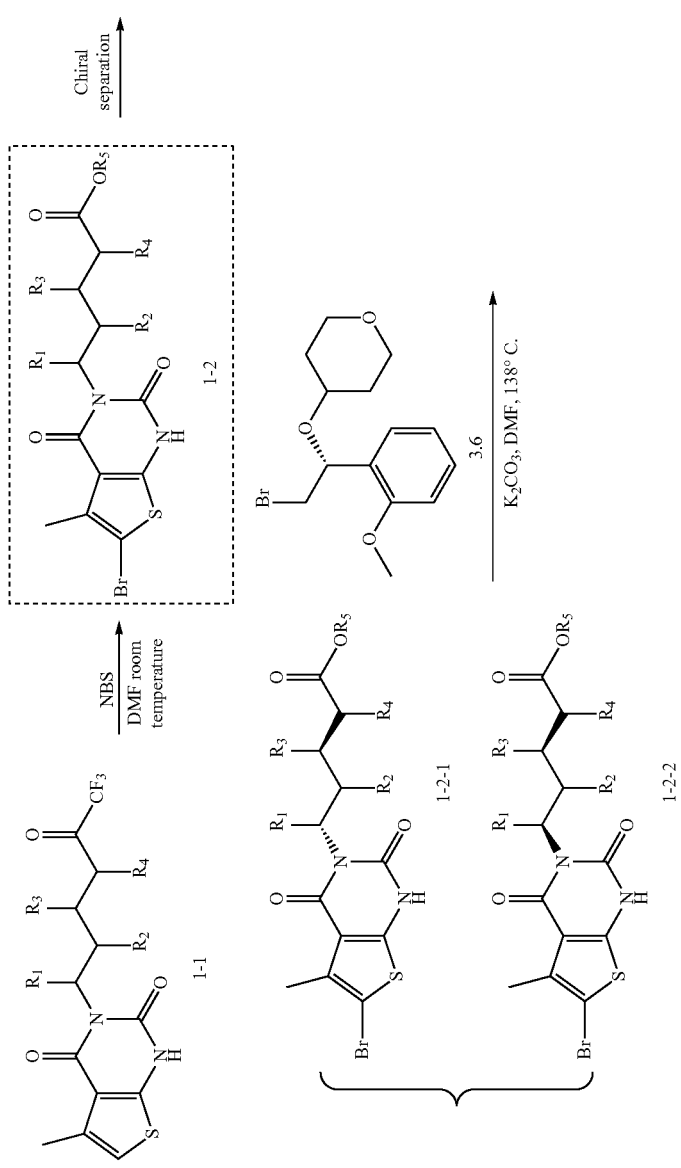

-continued
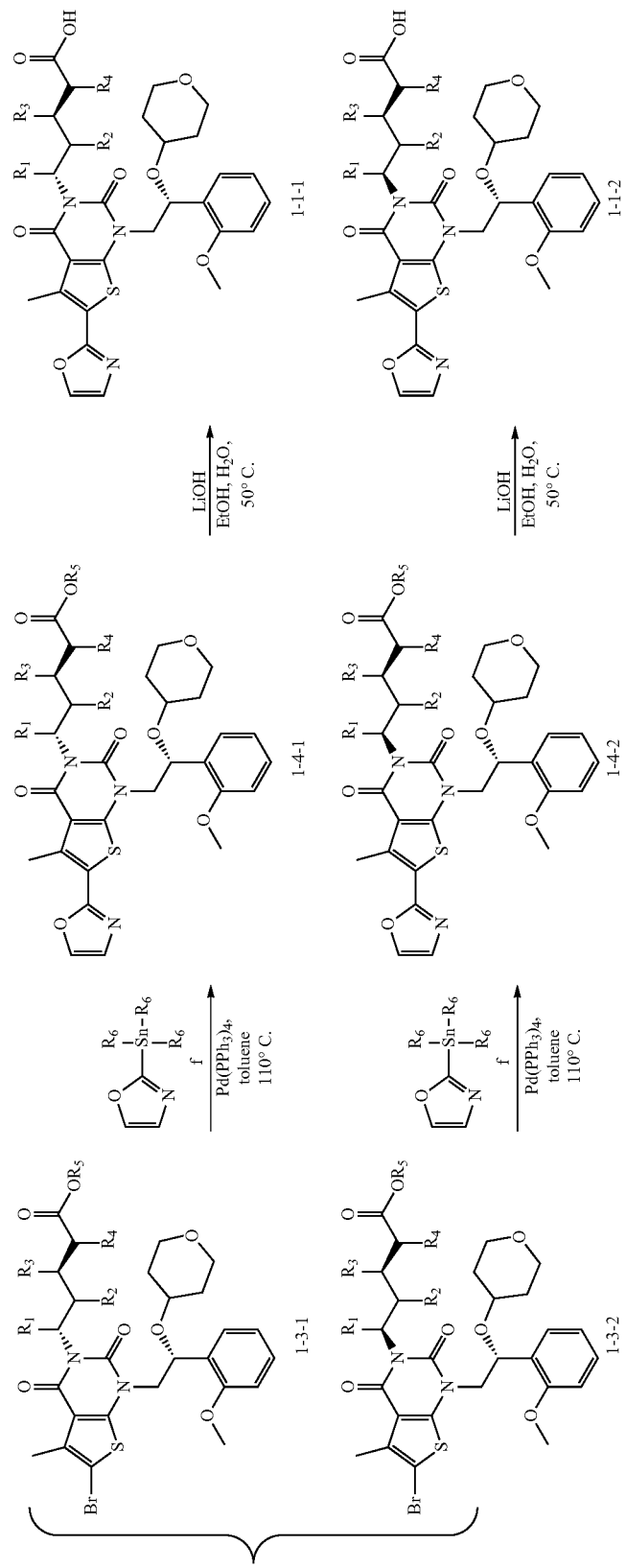

An intermediate I-1 can be prepared by using a method known in the prior art, and further reaction is conducted according to method G to obtain compounds of general formulas I-I-1 and I-I-2. $R_1$ is H, $C_{1-6}$ alkyl, $C_{1-6}$ haloalkyl, or $C_{1-6}$ alkoxy; $R_2$ is H, $C_{1-6}$ alkyl, $C_{1-6}$ haloalkyl, or $C_{1-6}$ alkoxy; $R_3$ is H, $C_{1-6}$ alkyl, $C_{1-6}$ haloalkyl, or $C_{1-6}$ alkoxy, or $R_1$ and $R_3$, together with a carbon atom bonded thereto, form 3-6 membered cycloalkyl; and $R_4$ is H, $C_{1-6}$ alkyl, $C_{1-6}$ haloalkyl, or $C_{1-6}$ alkoxy, or $R_4$ and $R_2$, together with a carbon atom bonded thereto, form 3-6 membered cycloalkyl. $R_5$ is $C_{1-6}$ alkyl. $R_6$ is $C_{3-6}$ alkyl.

Method E:

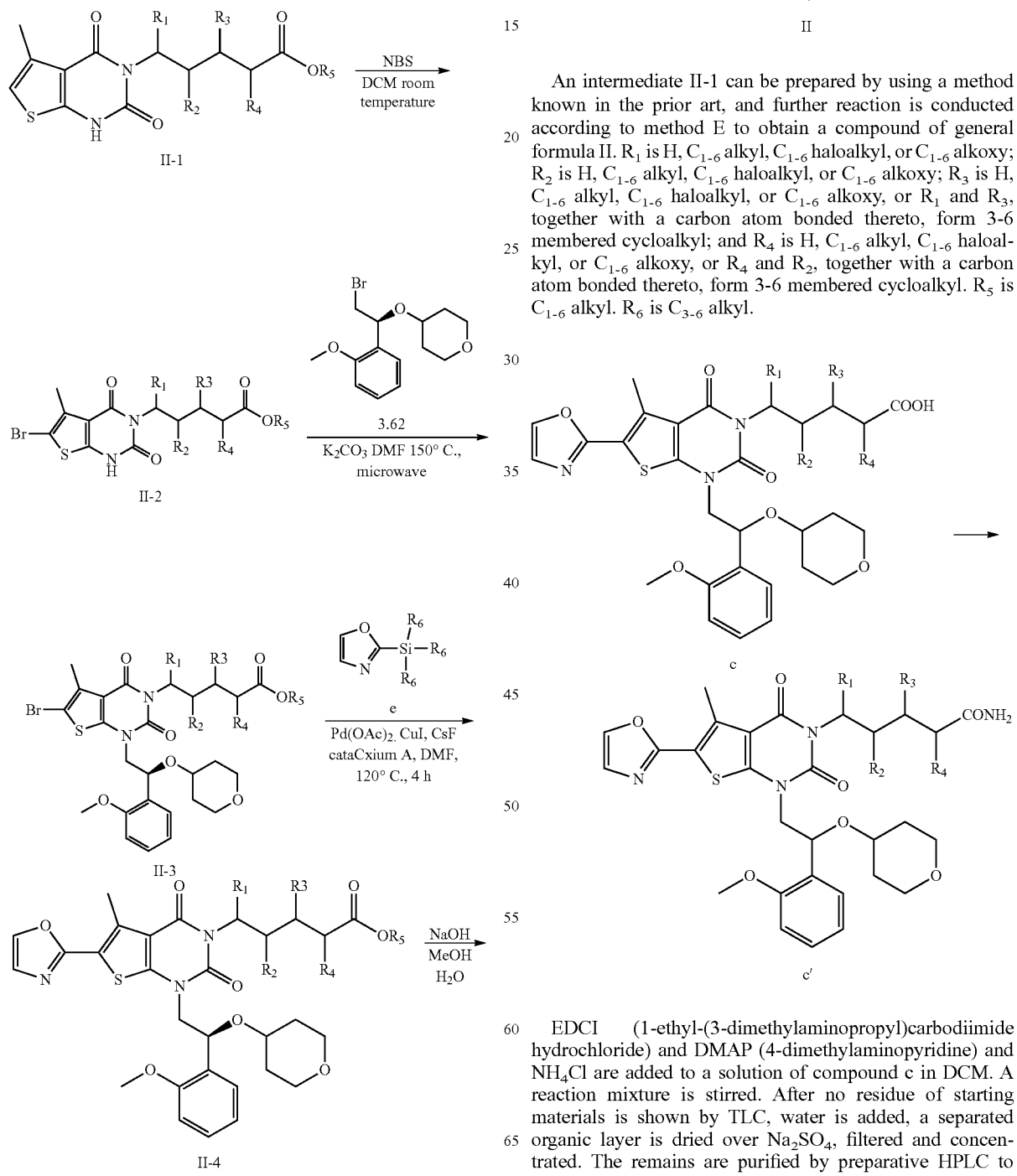

An intermediate II-1 can be prepared by using a method known in the prior art, and further reaction is conducted according to method E to obtain a compound of general formula II. $R_1$ is H, $C_{1-6}$ alkyl, $C_{1-6}$ haloalkyl, or $C_{1-6}$ alkoxy; $R_2$ is H, $C_{1-6}$ alkyl, $C_{1-6}$ haloalkyl, or $C_{1-6}$ alkoxy; $R_3$ is H, $C_{1-6}$ alkyl, $C_{1-6}$ haloalkyl, or $C_{1-6}$ alkoxy, or $R_1$ and $R_3$, together with a carbon atom bonded thereto, form 3-6 membered cycloalkyl; and $R_4$ is H, $C_{1-6}$ alkyl, $C_{1-6}$ haloalkyl, or $C_{1-6}$ alkoxy, or $R_4$ and $R_2$, together with a carbon atom bonded thereto, form 3-6 membered cycloalkyl. $R_5$ is $C_{1-6}$ alkyl. $R_6$ is $C_{3-6}$ alkyl.

EDCI (1-ethyl-(3-dimethylaminopropyl)carbodiimide hydrochloride) and DMAP (4-dimethylaminopyridine) and $NH_4Cl$ are added to a solution of compound c in DCM. A reaction mixture is stirred. After no residue of starting materials is shown by TLC, water is added, a separated organic layer is dried over $Na_2SO_4$, filtered and concentrated. The remains are purified by preparative HPLC to obtain a compound c' as a white solid.

In certain embodiments, the compound of formula c of the present invention is selected from Table 1.

TABLE 1

Exemplary compounds of formula c

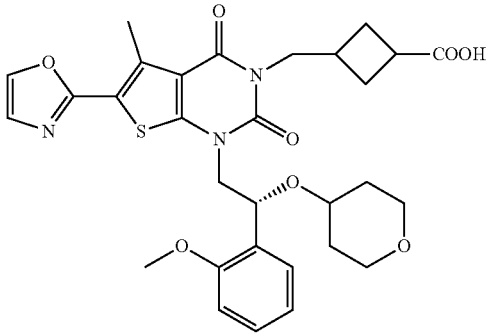 [SMILES: COc1ccccc1[C@H](Cn1c(=O)n(CC2CC(C(=O)O)C2)c(=O)c2c(C)c(-c3ncco3)sc21)OC1CCOCC1]

c-1

(R)-3-((1-(2-(2-methoxyphenyl)-2-((tetrahydro-2H-pyran-4-yl)oxy)ethyl)-5-methyl-6-(oxazol-2-yl)-2,4-dioxa-1,4-dihydrothieno[2,3-d]pyrimidine-3(2H)-yl)methyl)cyclobutane-1-carboxylic acid

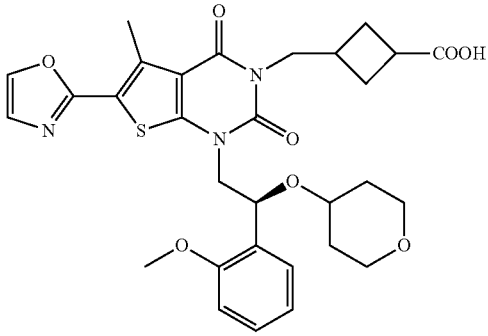 [SMILES: COc1ccccc1[C@@H](Cn1c(=O)n(CC2CC(C(=O)O)C2)c(=O)c2c(C)c(-c3ncco3)sc21)OC1CCOCC1]

c-2

(S)-3-((1-(2-(2-methoxyphenyl)-2-((tetrahydro-2H-pyran-4-yl)oxy)ethyl)-5-methyl-6-(oxazol-2-yl)-2,4-dioxa-1,4-dihydrothieno[2,3-d]pyrimidine-3(2H)-yl)methyl)cyclobutane-1-carboxylic acid

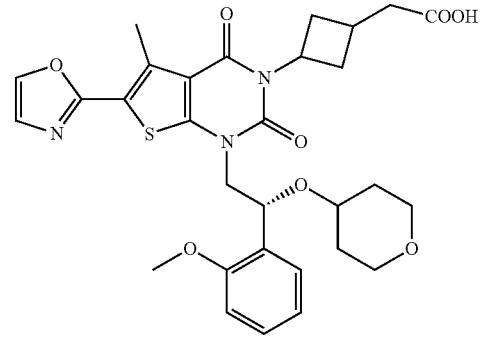 [SMILES: COc1ccccc1[C@H](Cn1c(=O)n(C2CC(CC(=O)O)C2)c(=O)c2c(C)c(-c3ncco3)sc21)OC1CCOCC1]

c-3

(R)-2-(3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidine-3(2H)-yl)cyclobutyl)acetic acid TABLE 1-continued Exemplary compounds of formula c

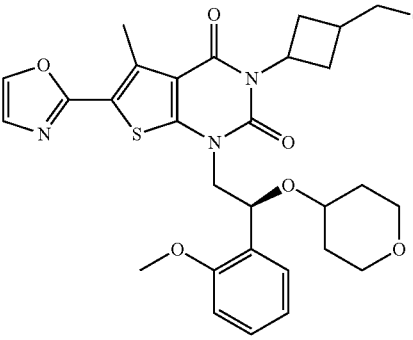

c-4

(S)-2-(3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidine-3(2H)-yl)cyclobutyl)acetic acid

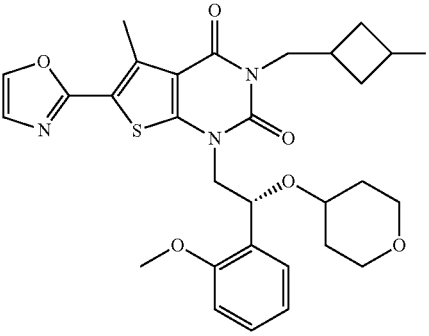

c'-1

(R)-3-((1-(2-(2-methoxyphenyl)-2-((tetrahydro-2H-pyran-4-yl)oxy)ethyl)-5-methyl-6-(oxazol-2-yl)-2,4-dioxa-1,4-dihydrothieno[2,3-d]pyrimidine-3(2H)-yl)methyl)cyclobutane-1-carboxamide

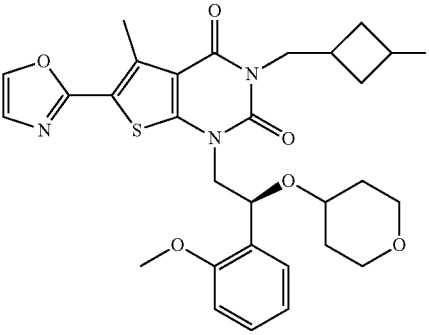

c'-2

(S)-3-((1-(2-(2-methoxyphenyl)-2-((tetrahydro-2H-pyran-4-yl)oxy)ethyl)-5-methyl-6-(oxazol-2-yl)-2,4-dioxa-1,4-dihydrothieno[2,3-d]pyrimidine-3(2H)-yl)methyl)cyclobutane-1-carboxamide

TABLE 1-continued

Exemplary compounds of formula c

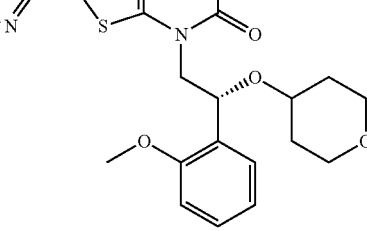

(R)-2-(3-(1-(2-(2-methoxyphenyl)-2-
((tetrahydro-2H-pyran-4-yl)oxy)ethyl)-5-
methyl-6-(oxazol-2-yl)-2,4-dioxo-1,4-
dihydrothieno[2,3-d]pyrimidine-3(2H)-
yl)cyclobutyl)acetamide  c'-3

(S)-2-(3-(1-(2-(2-methoxyphenyl)-2-
((tetrahydro-2H-pyran-4-yl)oxy)ethyl)-5-
methyl-6-(oxazol-2-yl)-2,4-dioxo-1,4-
dihydrothieno[2,3-d]pyrimidine-3(2H)-
yl)cyclobutyl)acetamide  c'-4

2-((1R,3R)-3-(1-((R)-2-(2-methoxyphenyl)-
2-((tetrahydro-2H-pyran-4-yl)oxy)
ethyl)-5-methyl-6-(oxazol-2-yl)-2,4-
dioxo-1,2-dihydrothieno[2,3-d]pyrimidine-
3(4H)-yl)cyclobutyl)acetic acid  c-3-1

2-((1S,3S)-3-(1-((R)-2-(2-methoxyphenyl)-
2-((tetrahydro-2H-pyran-4-yl)oxy)
ethyl)-5-methyl-6-(oxazol-2-yl)-2,4-dioxo-
1,2-dihydrothieno[2,3-d]pyrimidine-
3(4H)-yl)cyclobutyl)acetic acid  c-3-2

Example 1

Synthesis of Compound (R)-3-((1-(2-(2-methoxy-phenyl)-2-((tetrahydro-2H-pyran-4-yl)oxy)ethyl)-5-methyl-6-(oxazol-2-yl)-2,4-dioxo-1,2-dihydrothieno[2,3-d]pyrimidine-3(4H)-yl)methyl)cyclobutane Carboxylic Acid c-1

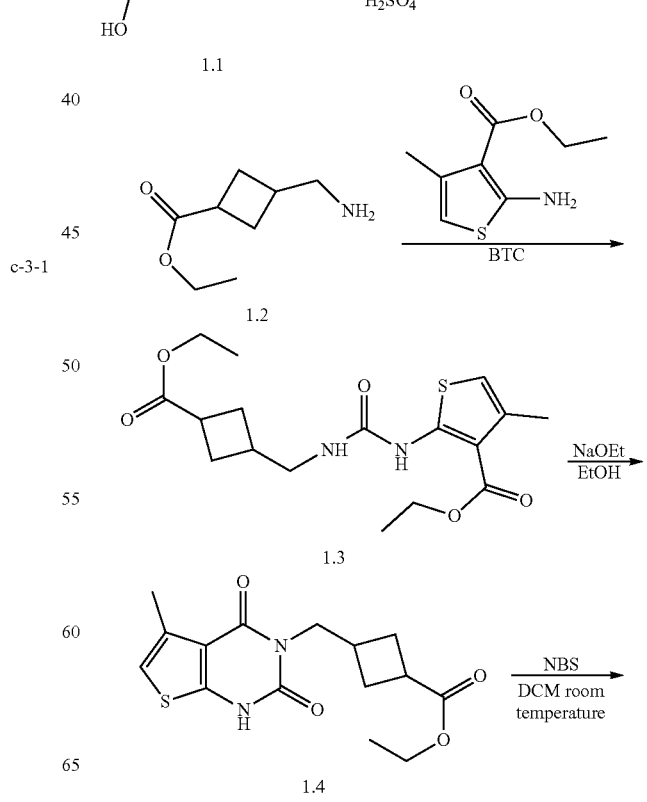

-continued

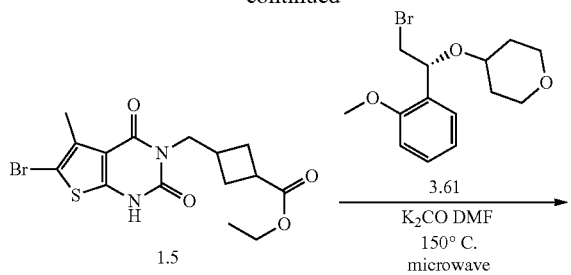

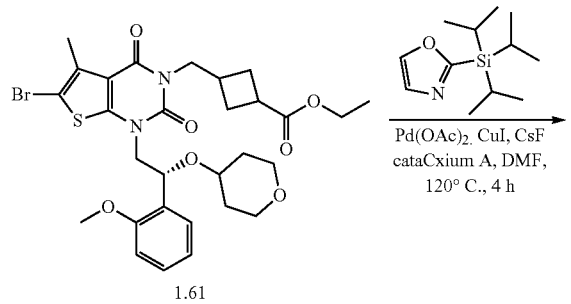

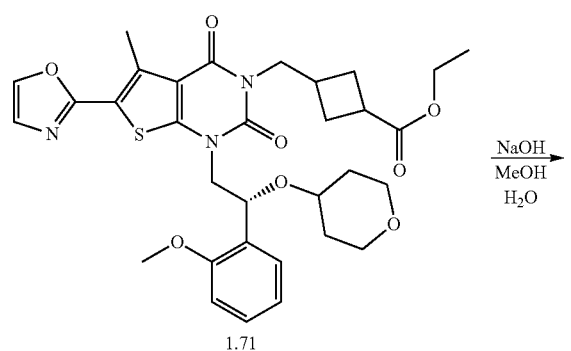

Synthesis of 3-(aminomethyl)cyclobutane Ethyl Formate 1.2

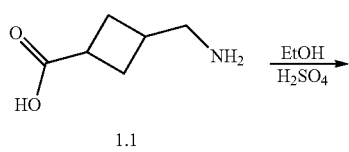

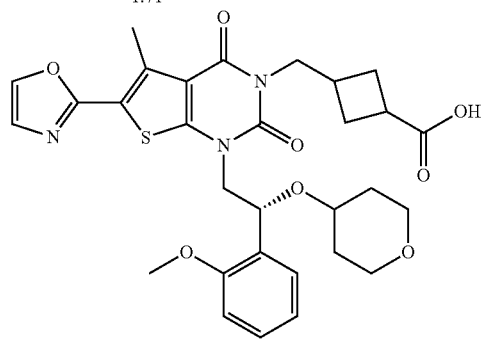

At 0° C., H$_2$SO$_4$ (0.1 g, 98%) was slowly added to a solution of compound 1.1 (1.0 g, 7.75 mmol) in EtOH (10 mL). A resulting mixture was stirred for 6 hours at 80° C. Then, a reaction mixture was cooled to room temperature, a saturated NaHCO$_3$ solution was added, and the mixture was extracted to THF. Organic layers were combined, dried over MgSO$_4$, filtered and concentrated to obtain a compound 1.2 (980 mg) as a yellow oil.

Mass spectrum: 158 [M+H]$^-$

Synthesis of 2-(3-((3-(ethyloxycarbonyl)cyclobutyl)methyl)uramido)-4-methylthiophene-3-ethyl Carboxylate 1.3

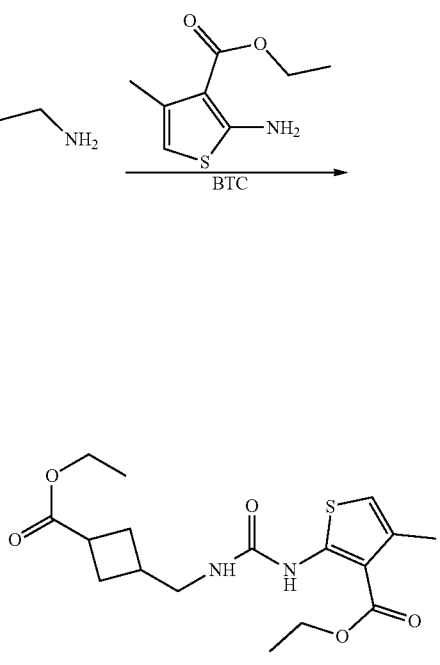

BTC (622 mg, 2.10 mmol) and pyridine (0.5 mL) were added to a solution of a compound 2-amino-4-methylthiophene-3-ethyl carboxylate (1.30 g, 7.01 mmol) in DCM (20 mL). The reaction mixture was stirred at room temperature for 2 hours, and then the compound 1.2 (1.0 g, 6.37 mmol) was added to the reaction mixture. A resulting mixture was stirred at room temperature for 2 hours. The reaction mixture was diluted with water, and extracted with EA. Organic layers were combined, washed with saline, dried over Na$_2$SO$_4$, filtered and concentrated. The remains were purified by silica-gel flash chromatography (PE/EA=4/1) to obtain a compound 1.3 (1.72 g) as a white solid.

Mass spectrum: 369 [M+H]$^-$

Synthesis of 3-((5-methyl-2,4-dioxo-1,2-dihydroth-
ieno[2,3-d]pyrimidine-3(4H)-yl)methyl)cyclobutane
Ethyl Formate 1.4

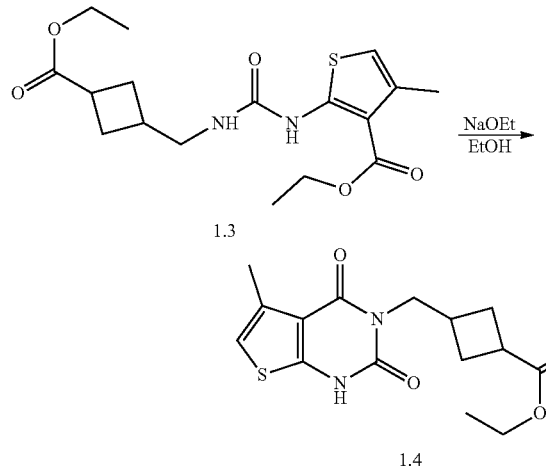

NaOEt (449 mg, 6.51 mmol) was added to a solution of the compound 1.3 (800 mg, 2.17 mmol) in EtOH (20 mL). The reaction mixture was stirred at room temperature for 8 hours, then diluted with H₂O (50 mL), and extracted with EA. Organic layers were combined, washed with saline, dried over Na₂SO₄, filtered and concentrated. The remains were purified by silica-gel flash chromatography (PE/EA=5/1) to obtain a compound 1.4 (510 mg) as a white solid.

Mass spectrum: 323 [M+H]⁺

Synthesis of 3-((6-bromo-5-methyl-2,4-dioxo-1,2-
dihydrothieno[2,3-d]pyrimidine-3(4H)-yl)methyl)
cyclobutaneethyl Carboxylate 1.5

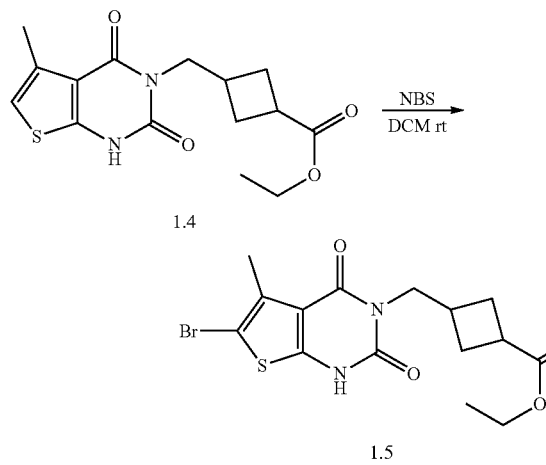

NBS (277 mg, 1.55 mmol) was added to a solution of the compound 1.4 (500 mg, 1.55 mmol) in DCM (10 mL). A reaction mixture was stirred at room temperature for 3 hours. Then, the reaction mixture was diluted with water, and extracted with EA. Organic layers were combined, washed with saline, dried over Na₂SO₄, filtered and concentrated. The remains were purified by silica-gel flash chromatography (PE/EA=5/1) to obtain a compound 1.5 (520 mg) as a white solid.

Mass spectrum: 401,403 [M+H]⁺

Synthesis of (R)-ethyl3-((6-bromo-1-(2-(2-methoxy-
phenyl)-2-((tetrahydro-2H-pyran-4-yl)oxy)ethyl)-5-
methyl-2,4-dioxo-1,2-dihydrothieno[2,3-d]pyrimi-
dine-3(4H)-yl)methyl)cyclobutane Carboxylate 1.61

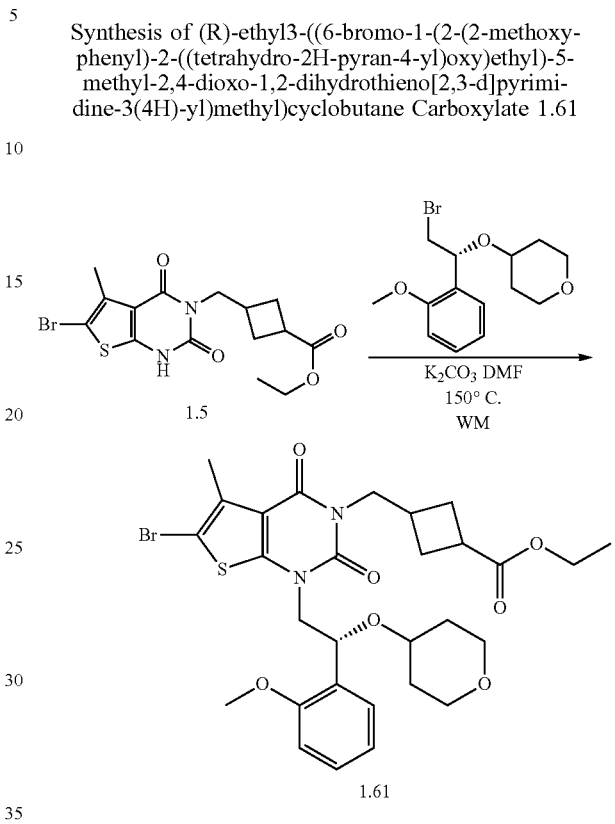

(R)-4-(2-bromo-1-(2-methoxyphenyl)ethyoxyl)tetra-hydro-2H-pyran3.61 (329 mg, 1.05 mmol) and K₂CO₃ (207 mg, 1.50 mmol) were added to a solution of the compound 1.5 (200 mg, 0.5 mmol) in DMF (3 mL). The reaction was stirred at 150° C. for 3 hours under microwave, then cooled to room temperature, diluted with H₂O, and extracted with EA. Organic layers were combined, washed with saline, dried over Na₂SO₄, filtered and concentrated. The remains were purified by silica-gel flash chromatography (PE/EA=4/1) to obtain a compound 1.61 (262 mg) as a white solid.

Mass spectrum: 635 [M+H]⁻

Synthesis of (R)-ethyl3-((1-(2-(2-methoxyphenyl)-
2-((tetrahydro-2H-pyran-4-yl)oxy)ethyl)-5-methyl-6-
(oxazol)-2-yl)-2,4-dioxo-1,2-dihydrothieno[2,3-d]
pyrimidine-3(4H)-yl)methyl)cyclobutane
Carboxylate 1.71

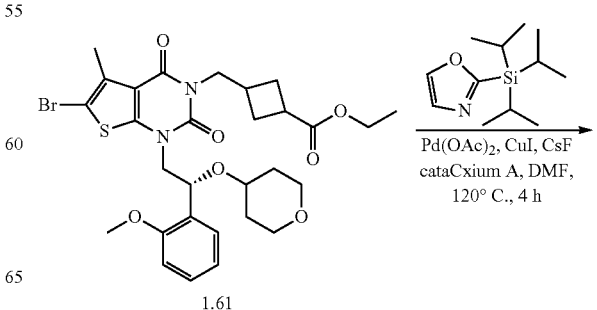

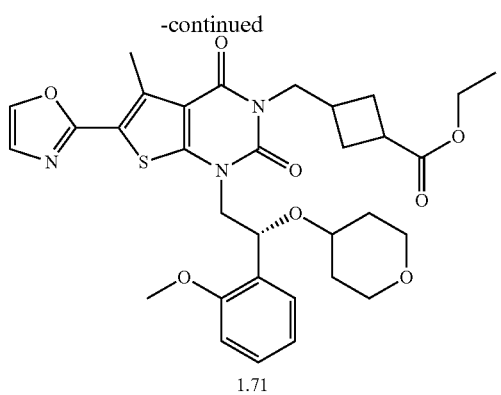

1.71

2-(triisopropylsilyl)oxazole (101.6 mg, 0.473 mmol), Pd(OAc)$_2$ (6.9 mg, 0.032 mmol), CuI (23.9 mg, 0.126 mmol), CsF (143.7 mg, 0.945 mmol) and CatCxium A (24.2 mg, 0.065 mmol) were added to a solution of the compound 1.61 (200 mg, 0.315 mmol) in DMF (6 mL). Then, a reaction mixture was stirred at 120° C. for 4 hours in the presence of nitrogen. The reaction mixture was cooled to room temperature, diluted with H$_2$O, and extracted with EA. Organic layers were combined, washed with saline, dried over Na$_2$SO$_4$, filtered and concentrated. The remains were purified by silica-gel flash chromatography (PE/EA=3/1) to obtain a compound 1.71 (106.5 mg) as a white solid.

Mass spectrum: 624 [M+H]$^-$

Synthesis of (R)-3-((1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidine-3(4H)-yl)methyl)cyclobutane Carboxylic Acid c-1

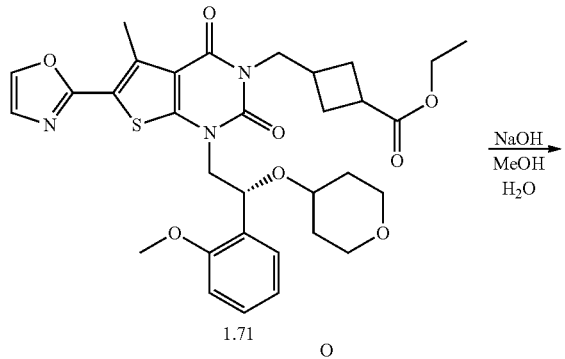

NaOH (19.3 mg, 0.482 mmol) was added to a solution of the compound 1.71 (100 mg, 0.161 mmol) in MeOH (3 mL) and water (1 mL). A reaction mixture was stirred at 40° C. for 2 hours. The pH of the reaction mixture was adjusted to 7 with 5% HCl, and extracted with EA. Organic layers were combined, washed with saline, dried over Na$_2$SO$_4$, filtered and concentrated to obtain the remains which were purified by preparative HPLC to obtain a compound c-1 (52.5 mg) as a white solid.

Mass spectrum: 596 [M+H]$^-$ $^1$H NMR (400 MHz, DMSO-d$_6$) δ 11.95 (br s, 1H), 8.23 (s, 1H), 7.48 (d, J=7.2 Hz, 1H), 7.33-7.29 (m, 1H), 7.31-7.29 (m, 1H), 7.05-6.95 (m, 1H), 6.51 (s, 1H), 5.31 (d, J=5 Hz, 1H), 4.10-4.02 (m, 3H), 3.96 (s, 3H), 3.74-3.49 (m, 2H), 3.34-3.32 (m, 1H), 3.31-3.30 (m, 2H), 2.89 (s, 31H), 2.39-2.37 (m, 2H), 2.32-2.17 (m, 2H), 2.11-2.08 (m, 2H), 1.32-1.23 (m, 4H).

Example 2

Synthesis of (S)-3-((1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidine-3(4H)-yl)methyl)cyclobutane Carboxylic Acid c-2

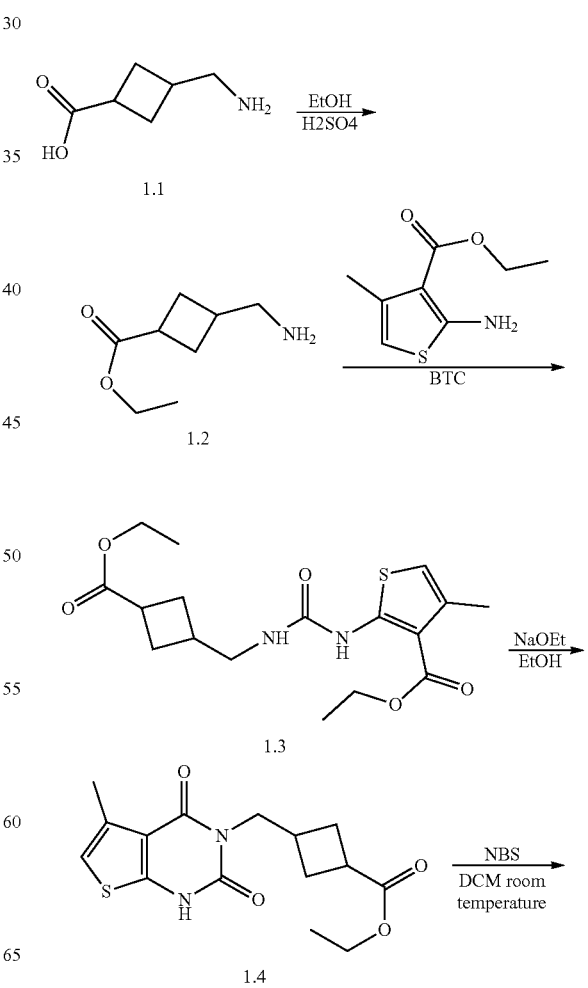

-continued

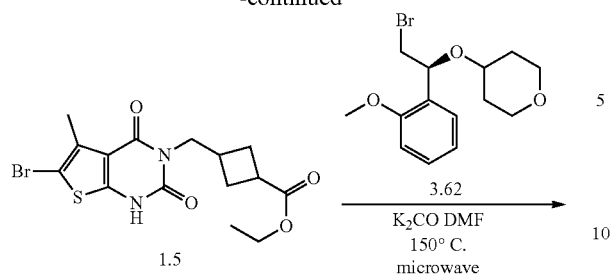

K$_2$CO DMF
150° C.
microwave

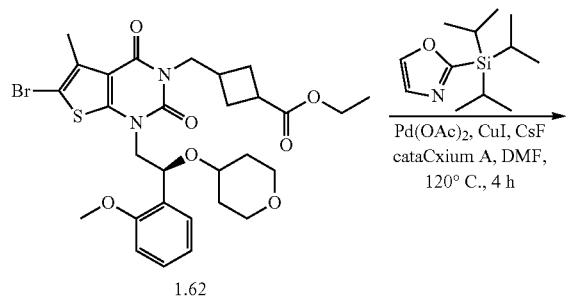

Pd(OAc)$_2$, CuI, CsF
cataCxium A, DMF,
120° C., 4 h

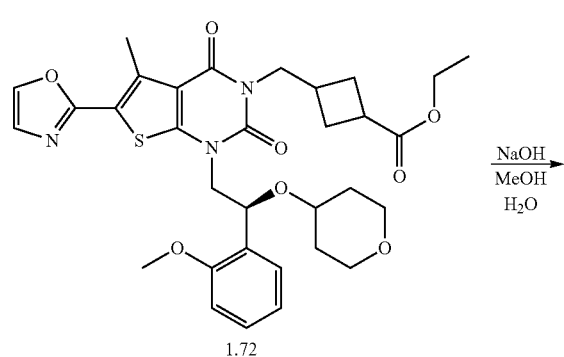

NaOH
MeOH
H$_2$O

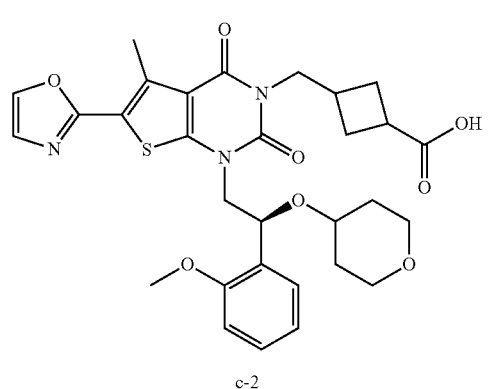

c-2

For the synthesis of c-2, a reference can be similarly referred to the method for synthesizing c-1.

Example 3

Synthesis of Compound (R)-2-(3-(1-(2-(2-methoxyphenyl)-2-((tetrahydro-2H-pyran-4-yl)oxy)ethyl)-5-methyl-6-(oxazol-2-yl)-2,4-dioxy-1,2-dihydrothieno[2,3-d]pyrimidine-3(4H)-yl)cyclobutyl)acetic Acid c-3

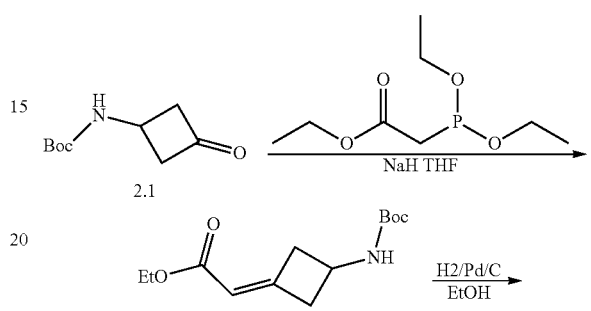

NaH THF

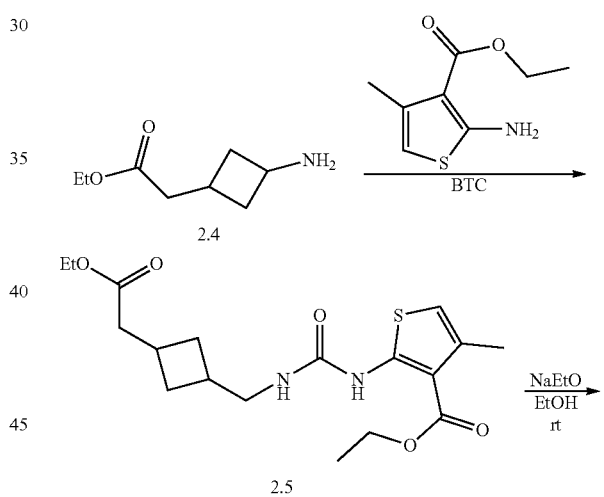

BTC

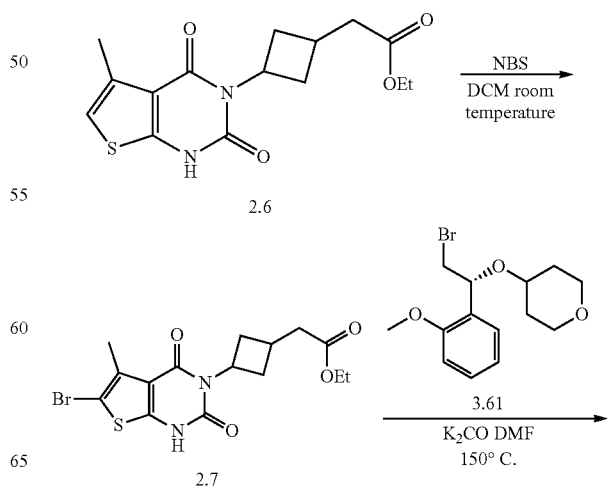

NaEtO
EtOH
rt

NBS
DCM room temperature

K$_2$CO DMF
150° C.

-continued

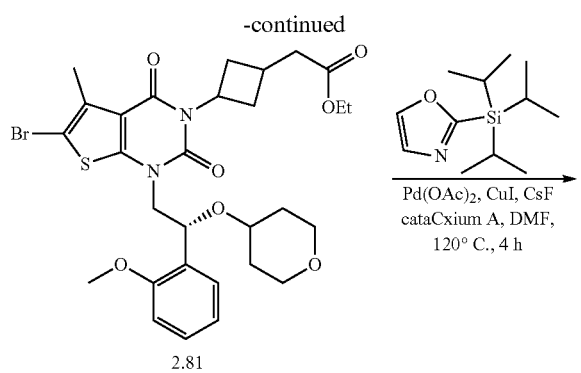

2.81

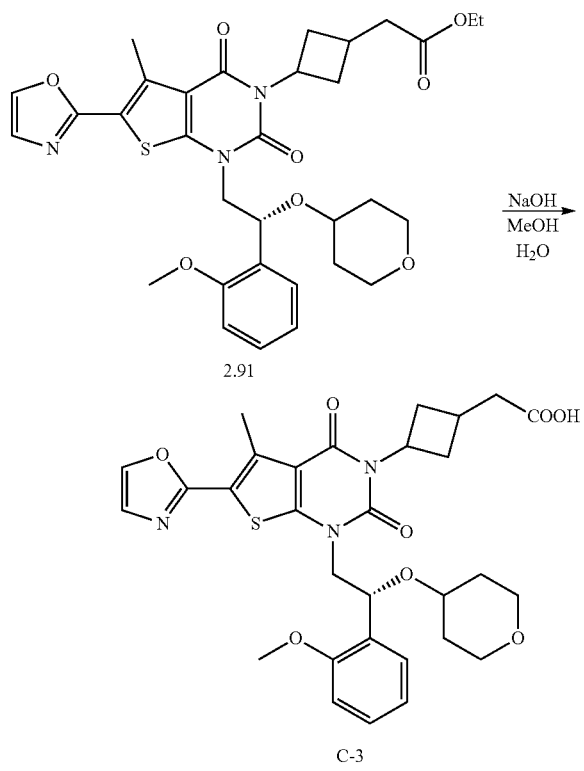

2.91

C-3

Synthesis of 2-(3-((t-butyloxycarbonyl)amino)cyclobutylene)ethyl Acetate 2.2

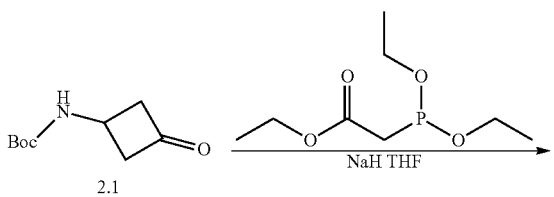

2.1

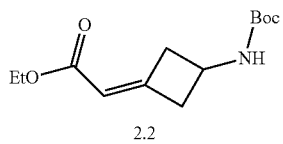

2.2

At 0° C., NaH (230.9 mg, 5.77 mmol) was added to a solution of 2-(diethyoxylphosphino)ethyl acetate (1.0 g, 4.81 mmol) in THF (20 mL). The reaction mixture was stirred at room temperature for 1 hour, and then, the compound 2.1 (978.8 mg, 5.29 mmol) was added to the reaction mixture. The resulting mixture was stirred at room temperature for 6 hours, then diluted with water, and extracted with EA. Organic layers were combined, washed with saline, dried over Na$_2$SO$_4$, filtered and concentrated. The remains were purified by silica-gel flash chromatography (PB/BA=6/1) to obtain a compound 2.2 (1.05 g) as a white solid.

Mass spectrum: 256 [M+H]$^-$

Synthesis of 2-(3-((t-butyloxycarbonyl)amino)cyclobutyl)ethyl Acetate 2.3

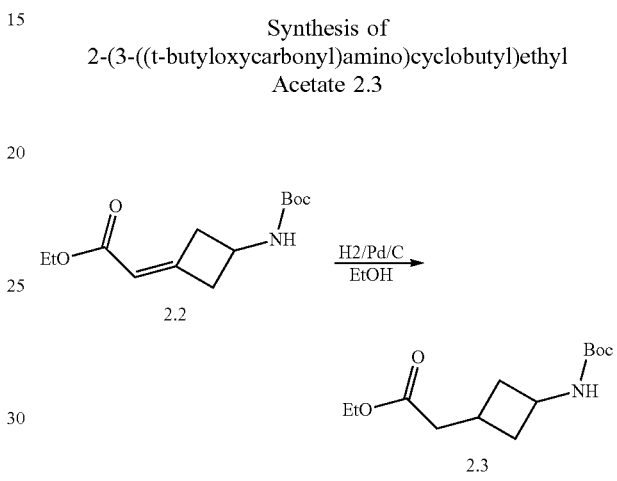

2.3

10% Pd/C (80 mg) was added to a solution of the compound 2.2 (800 mg, 3.13 mmol) in EtOH (15 mL). A reaction mixture was stirred for 8 hours at room temperature in the presence of H$_2$ (1 atm). Diisopropyl ether wad added to the reaction mixture, which was then filtered to collect a compound 2.3 (750 mg) as a yellow oil.

Mass spectrum: 258 [M+H]$^-$

Synthesis of 2-(3-aminocyclobutyl)ethyl Acetate 2.4

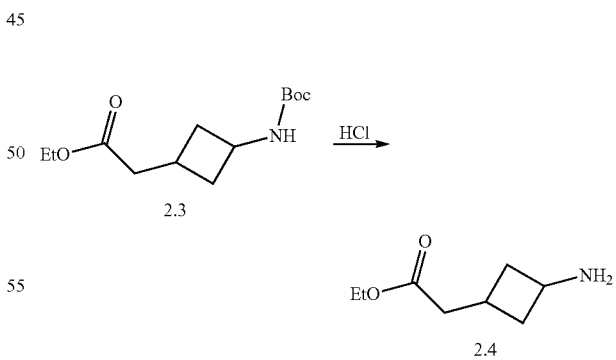

2.4

A solution of 4N hydrochloric acid in dioxane (10 mL) was added to a solution of the compound 2.3 (650 mg, 2.53 mmol) in 1,4-dioxane (10 mL). A reaction mixture was stirred at room temperature overnight. Diethyl ether was added to the reaction mixture, which was then filtered to harvest a compound 2.4 (385 mg) as a white solid.

Mass spectrum: 158 [M+H]$^-$

Synthesis of 2-(3-(3-(2-ethyoxyl-2-oxyethyl)cyclobutyl)uramido)-4-methylthiophene-3-ethyl Carboxylate 2.5

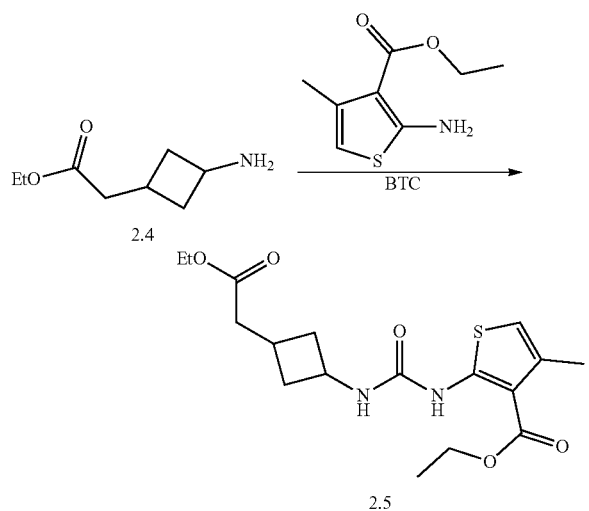

BTC (312 mg, 1.05 mmol) and pyridine (0.5 mL) were added to a coluation of the compound 2-amino-4-methylthiophene-3-ethyl carboxylate (647 mg, 3.50 mmol) in DCM (20 mL). The reaction mixture was stirred at room temperature for 2 hours, then the compound 2.4 (500 mg, 3.18 mmol) was added to the reaction mixture. A resulting mixture was stirred at room temperature for 2 hours. The reaction mixture was diluted with water, and extracted with EA. Organic layers were combined, washed with saline, dried over $Na_2SO_4$, filtered and concentrated. The remains were purified by silica-gel flash chromatography (PE/EA=4/1) to obtain a compound 2.5 (890 mg) as a white solid.

Mass spectrum: 369 $[M+H]^-$

Synthesis of 2-(3-(5-methyl-2,4-dioxy-1,2-dihydrothieno[2,3-d]pyrimidine-3(4H)-yl)cyclobutyl) ethyl Acetate 2.6

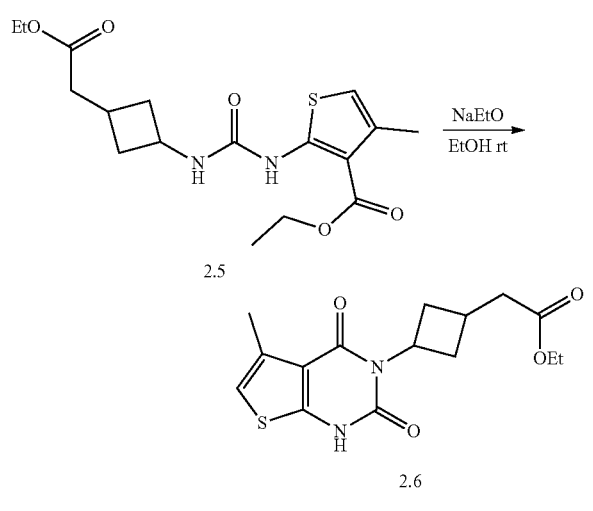

NaOEt (281 mg, 4.07 mmol) was added to a solution of the compound 2.5 (500 mg, 1.36 mmol) in EtOH (10 mL). After being stirred at room temperature for 8 hours, the reactants were diluted with water, and extracted with EA. Organic layers were combined, washed with saline, dried over $Na_2SO_4$, filtered and concentrated. The remains were purified by silica-gel flash chromatography (PE/EA=5/1) to obtain a compound 2.6 (368 mg) as a white solid.

Mass spectrum: 323 $[M+H]^+$

Synthesis of 2-(3-(6-bromo-5-methyl-2,4-dioxy-1,2-dihydrothieno[2,3-d]pyrimidine-3(4H)-yl)cyclobutyl)ethyl Acetate 2.7

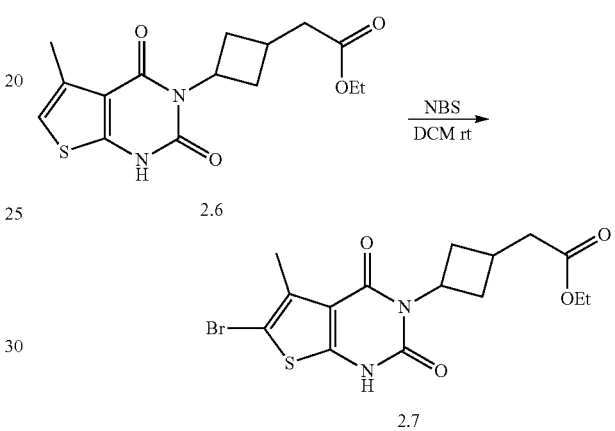

NBS (204.5 mg, 1.14 mmol) was added to a solution of the compound 2.6 (368 mg, 1.14 mmol) in DCM (10 mL). A reaction mixture was stirred at room temperature for 3 hours. Then, the reaction mixture was diluted with water, and extracted with EA. Organic layers were combined, washed with saline, dried over $Na_2SO_4$, filtered and concentrated. The remains were purified by silica-gel flash chromatography (PE/EA=5/1) to obtain a compound 2.7 (410 mg) as a white solid.

Mass spectrum: 401,403 $[M+H]^+$

Synthesis of (R)-ethyl2-(3-(6-bromo-1-(2-(2-methoxyphenyl)-2-((tetrahydro-2H-pyran-4-yl)oxy)ethyl)-5-methyl)ethyl-2,4-dioxy-1,2-dihydrothieno[2,3-d]pyrimidine-3(4H)-yl)cyclobutyl)acetate 2.81

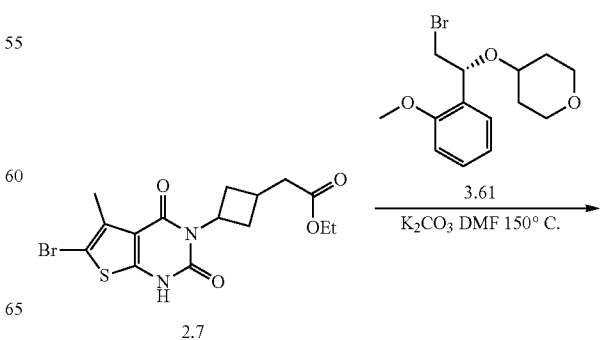

-continued

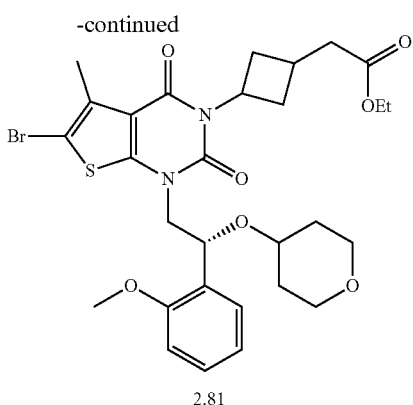

2.81

(R)-4-(2-bromo-1-(2-methoxyphenyl)ethyoxyl)tetrahydro-2H-pyrane 3.61 (688.6 mg, 2.2 mmol) and K$_2$CO$_3$ (414 mg, 3.0 mmol) were added to a solution of the compound 2.7 (400 mg, 1.0 mmol) in DMF (5 mL). The reactants were stirred at 150° C. for 3 hours under microwave, then cooled to room temperature, diluted with H$_2$O, and extracted with EA. Organic layers were combined, washed with saline, dried over Na$_2$SO$_4$, filtered and concentrated. The remains were purified by silica-gel flash chromatography (PE/EA=4/1) to obtain a compound 2.81 (412 mg) as a white solid.

Mass spectrum: 635 [M+H]$^+$

Synthesis of (R)-ethyl2-(3-(1-(2-(2-methoxyphenyl)-2-((tetrahydro-2H-pyran-4-yl)oxy)ethyl)-5-methyl-6-(oxazol-2-yl)-2,4-dioxy-1,2-dihydrothieno[2,3-d]pyrimidine-3(4H)-yl)cyclobutyl)acetate 2.91

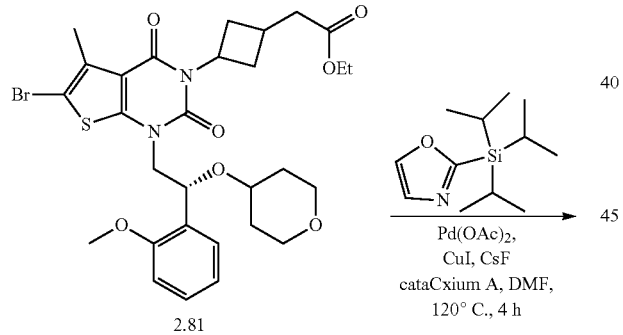

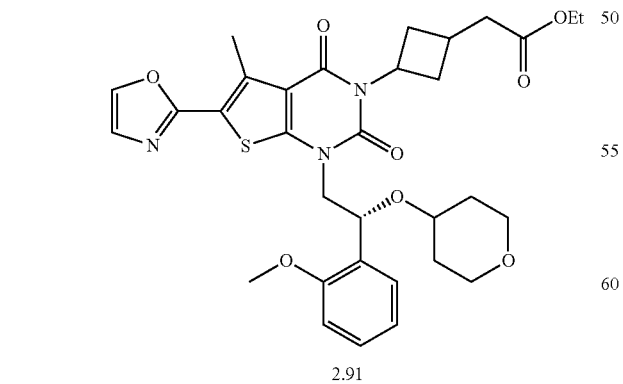

2.91

2-(triisopropylsilyl)oxazole (101.6 mg, 0.473 mmol), Pd(OAc)$_2$ (6.9 mg, 0.032 mmol), CuI (23.9 mg, 0.126 mmol), CsF (143.7 mg, 0.945 mmol) and CatCxium A (24.2 mg, 0.065 mmol) were added to a solution of the compound 2.81 (200 mg, 0.315 mmol) in DMF (6 mL). Then, a reaction mixture was stirred at 120° C. for 4 hours. The reaction mixture was cooled to room temperature, diluted with H$_2$O, and extracted with EA. Organic layers were combined, washed with saline, dried over Na$_2$SO$_4$, filtered and concentrated. The remains were purified by silica-gel flash chromatography (PE/EA=3/1) to obtain a compound 2.91 as a white solid.

Mass spectrum: 624 [M+H]$^-$

Synthesis of Compound (R)-2-(3-(1-(2-(2-methoxyphenyl)-2-((tetrahydro-2H-pyran-4-yl)oxy)ethyl)-5-m ethyl-6-(oxazol-2-yl)-2,4-dioxy-1,2-dihydrothieno[2,3-d]pyrimidine-3(4H)-yl)cyclobutyl)acetic Acid c-3

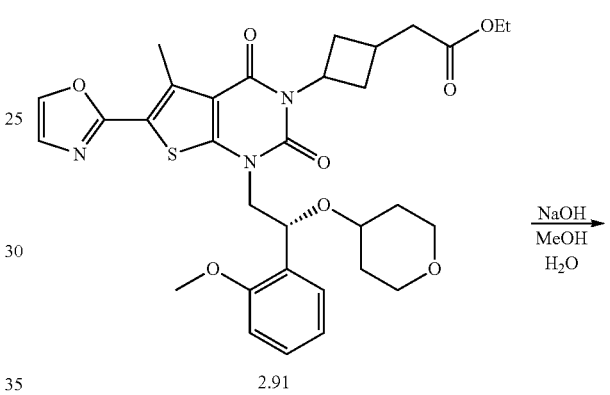

2.91

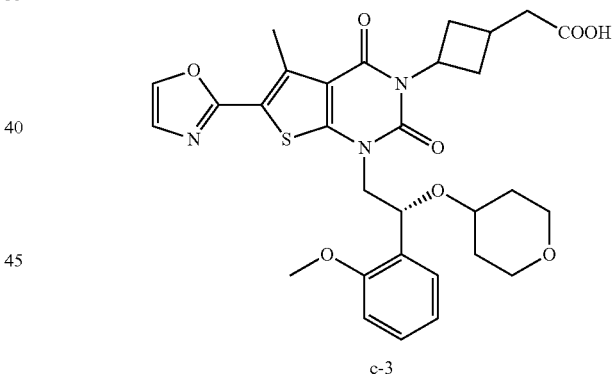

c-3

NaOH (17.3 mg, 0.433 mmol) was added to a solution of the compound 2.91 (90 mg, 0.145 mmol) in MeOH (3 mL) and water (1 mL). A reaction mixture was stirred at 40° C. for 2 hours. The pH of the reaction mixture was adjusted to 7 with 5% HCl, and extracted with EA. Organic layers were combined, washed with saline, dried over Na$_2$SO$_4$, filtered and concentrated to obtain the reamins, which were purified by HPLC to obtain a compound c-3 as a white solid.

Mass spectrum: 596 [M+H]$^-$ $^1$H NMR (400 MHz, CDCl$_3$) δ 7.70 (s, 1H), 7.56-7.52 (m, 1H), 7.59-7.57 (m, 1H), 7.27 (d, J=4.0 Hz, 1H), 7.21 (s, 1H), 7.04-7.00 (m, 1H), 6.86 (d, J=8.0 Hz, 1H), 5.40-5.36 (m, 1H), 5.14 (s, 1H), 4.16-4.06 (m, 2H), 3.85 (s, 3H), 3.76-3.68 (m, 2H), 3.41 (d, J=4.0 Hz, 1H), 3.34-3.31 (m, 3H), 2.69-2.58 (m, 4H), 2.13 (s, 1H), 1.82-1.79 (m, 4H), 1.70 (d, J=5.6 Hz, 2H), 1.58 (d, J=9.2 Hz, 2H).

Example 4

Synthesis of Compound c'-3

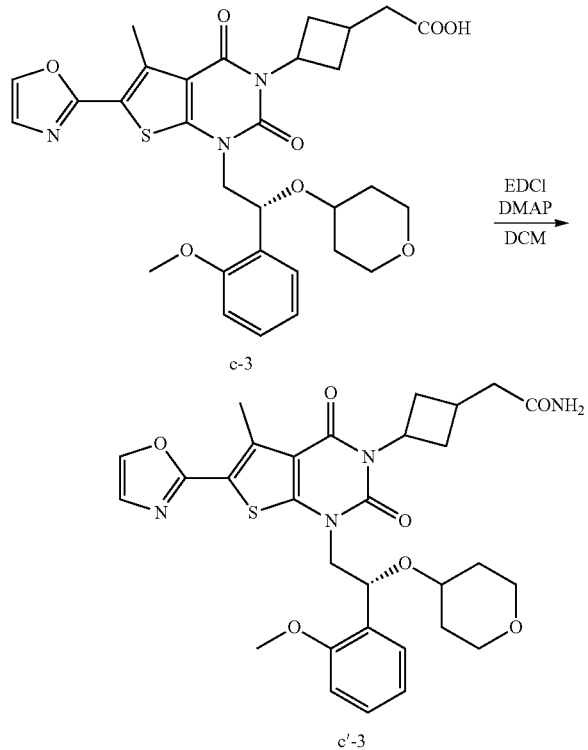

EDCI (27 mg, 0.14 mmol) and DMAP (25.8 mg, 0.21 mmol) and NH₄Cl (15 mg, 0.28 mmol) were added to a solution of the compound c-3 (59.6 mg, 0.10 mmol) in 1.2 mL DCM. A reaction mixture was stirred at 40° C. for 2 hours. After no residue of starting materials was shown by TLC, 5 mL of water was added, a separated organic layer was dried over Na₂SO₄, filtered and concentrated. The remains are purified by preparative HPLC to obtain a compound c'-3 (27.8 mg) as a white solid.

Mass spectrum: 595 [M+H]⁻

Example 5

Synthesis of Compound (S)-ethyl 2-(3-(1-(2-(2-methoxyphenyl)-2-((tetrahydro-2H-pyran-4-yl)oxy)ethyl)-5-methyl-6-(oxazol-2-yl)-2,4-dioxy-1,2-dihydrothieno[2,3-d]pyrimidine-3(4H)-yl)cyclobutyl)acetate c-4

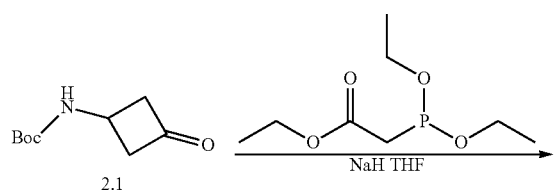

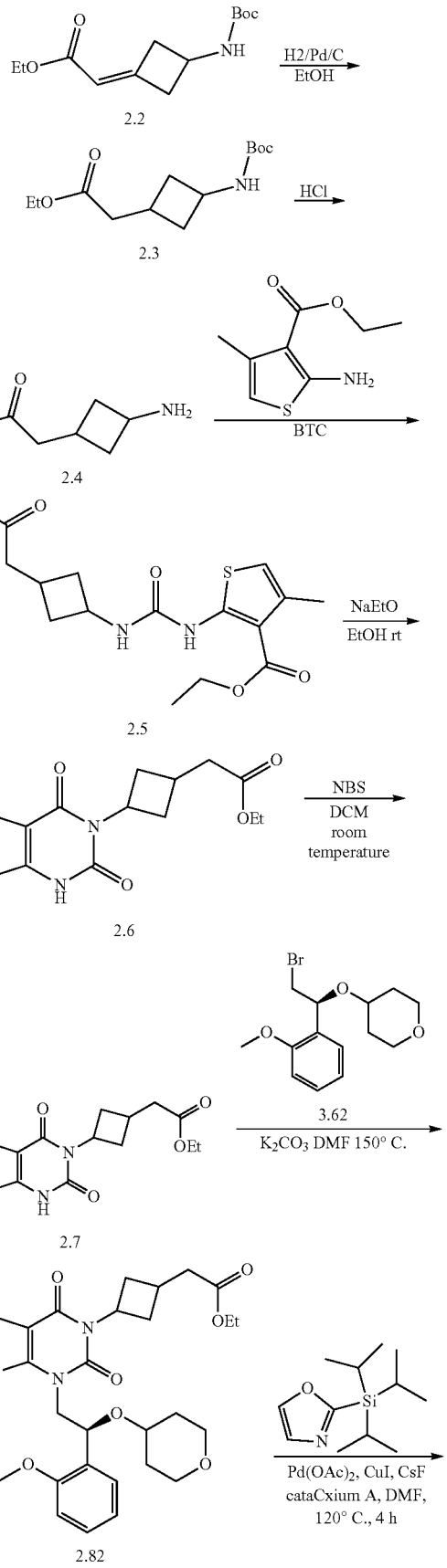

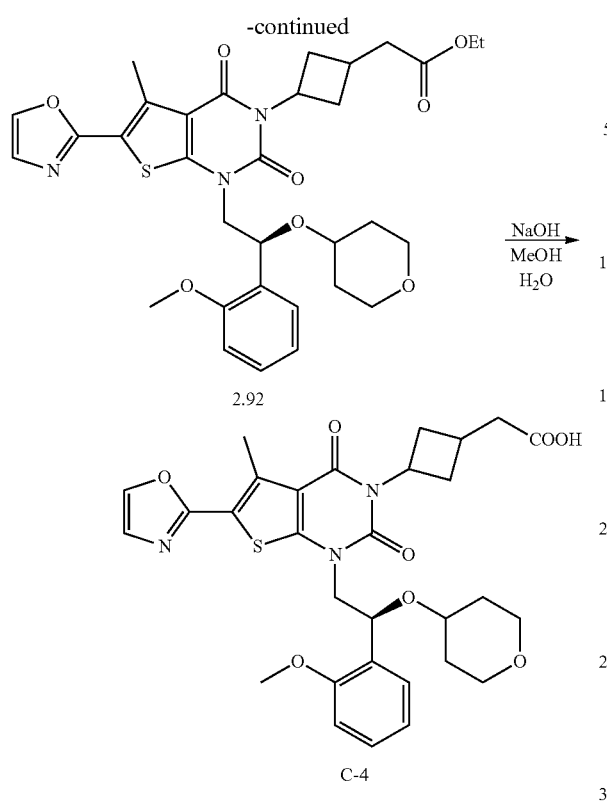

For the synthesis of c-4, a reference can be similarly referred to the method for synthesizing c-3.

Example 6

Synthesis of 2-(triisopropylsilyl)oxazole

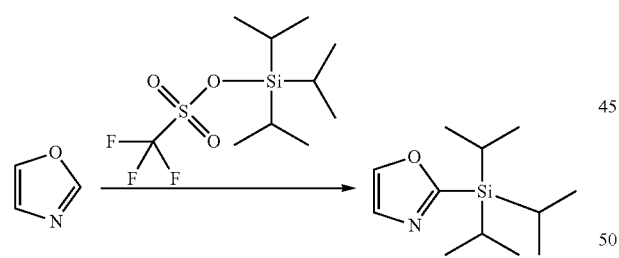

A solution of n-butyllithium (11.6 mL, 29 mmol, in 2.5 M ethane solution) was dropwise added to a solution of oxazole (1.0 g, 14.5 mmol) in THF (15 mL) at −78° C. in the presence of $N_2$. After the reaction mixture was stirred for another 45 minutes at −78° C., triisopropylsilyltrifluoromethanesulfonate (6.65 g, 21.8 mmol) was slowly added to the reaction mixture at −78° C. After the addition was completed, the reaction mixture was slowly heated to room temperature, and stirred for 12 hours. The reaction mixture was diluted with water, and extracted with EA. The organic layers were combined, washed with saline, and dried over $Na_2SO_4$, filtered and concentrated. The remains were purified by silica-gel flash chromatography (PE/EA=20/1) to obtain a compound 2-(triisopropylsilyl)oxazol (1.1 g) as a yellow oily matter.

Example 7

Chiral Separation

The compound 2.7 was chirally separated into 2.7-1 (2.0 g, a trans-isomer) and 2.7-2 (4.2 g, a cis-isomer).

Mass spectrum: 401, 403 [M+H]$^+$

Synthesis of 2-((1R,3r)-3-(6-bromo-1-((R)-2-(2-methoxyphenyl)-2-((tetrahydro-2H-pyran-4-yl)oxy)ethyl)-5-methyl-2,4-dioxo-1,2-dihydrothieno[2,3-d]pyrimidine-3(4H)-yl)cyclobutyl)ethyl Acetate 2.81-1

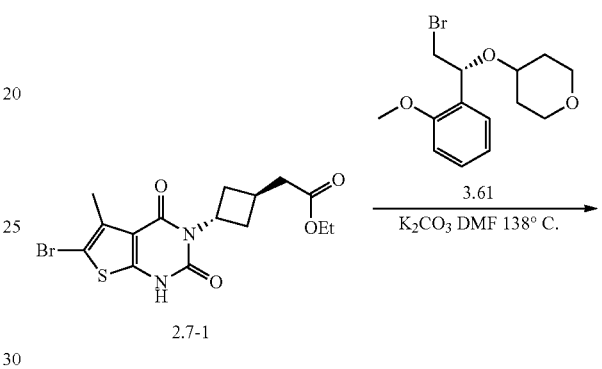

(R)-4-(2-bromo-1-(2-methoxyphenyl)ethyoxyl)tetrahydro-2H-pyrane 3.61 (2.0 g, 6.4 mmol) and $K_2CO_3$ (1.5 g, 11 mmol) were added to a solution of the compound 2.7-1 (1.4 g, 3.5 mmol) in DMF (20 mL). The reactants were stirred for 6 hours at 138° C. in an airtight tube, then cooled to room temperature, diluted with $H_2O$, and extracted with EA. Organic layers were combined, washed with saline, dried over $Na_2SO_4$, filtered and concentrated. The remains were purified by silica-gel flash chromatography (PE/EA=10/1) to obtain a compound 2.81-1 (1.6 g) as a colorless oil.

Mass spectrum: 637 [M+H]$^+$

Synthesis of 2-((1R,3r)-3-(1-((R)-2-(2-methoxyphenyl)-2-((tetrahydro-2H-pyran-4-yl)oxy)ethyl)-5-methyl-6-(oxazol-2-yl)-2,4-dioxp-1,2-dihydrothieno[2,3-d]pyrimidine-3(4H)-yl)cyclobutyl)ethyl Acetate 2.91-1

Synthesis of Compound 2-((1R,3r)-3-(1-((R)-2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidine-3(4H)-yl)cyclobutyl) acetic Acid c-3-1

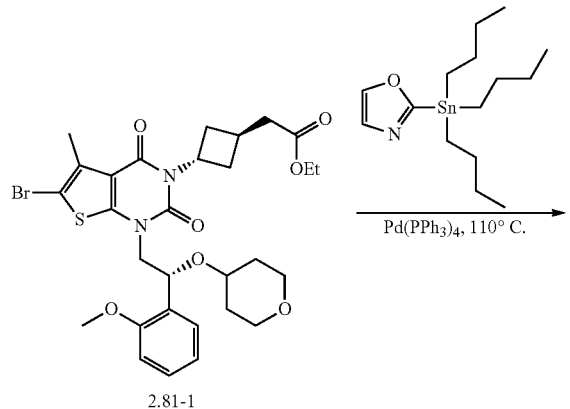

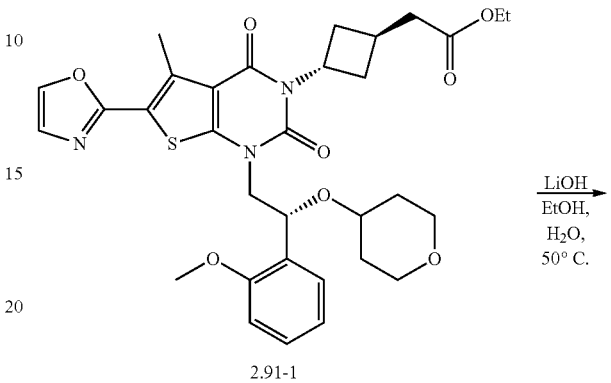

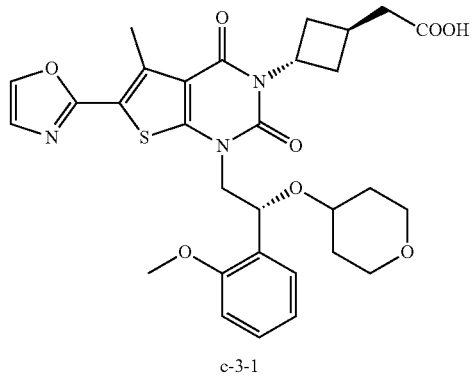

c-3-1

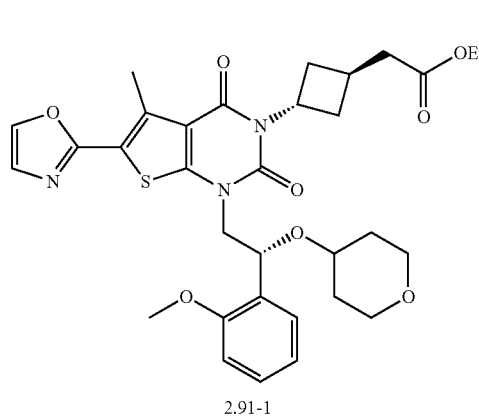

2.91-1

2-(tributylstannyl)oxazol (1.7 g, 4.7 mmol) and Pd(PPh₃)₄ (0.5 g, 0.4 mmol) were added to a solution of the compound 2.81-1 (1 g, 1.6 mmol) in toluene (20 mL). Then, the reaction mixture was stirred for 10 hours at 110° C. The reaction mixture was cooled to room temperature, diluted with H₂O, and extracted with EA. Organic layers were combined, washed with saline, dried over Na₂SO₄, filtered and concentrated. The remains were purified by silica-gel flash chromatography (PE/EA=3/1) to obtain a compound 2.91-1 (700 mg) as a yellow solid.

Mass spectrum: 624 [M+H]⁻

LiOH (300 mg, 7.1 mmol) was added to a solution of the compound 2.91-1 (500 mg, 0.8 mmol) in EtOH (15 mL) and water (3 mL). The reaction mixture was stirred at 50° C. for 2 hours. The pH of the reaction mixture was adjusted to 7 with 5% HCl, and extracted with EA. Organic layers were combined, washed with saline, dried over Na₂SO₄, filtered and concentrated to obtain the remains, which were purified by silica-gel flash chromatography (DCM/MeOH=50/1) to obtain a compound c-3-1 (300 mg) as a white solid.

¹H NMR (400 MHz, DMSO-d₆) δ:11.99 (br s, 1H), 8.22 (s, 1H), 7.50-7.48 (m, 1H), 7.38 (d, J=0.8 Hz, 1H), 7.32-7.27 (m, 1H), 7.05-6.95 (m, 2H), 5.52-5.43 (m, 1H), 5.31 (t, J=6.4 Hz, 1H), 4.10-3.95 (m, 2H), 3.78 (s, 3H), 3.60-3.55 (m, 1H), 3.52-3.49 (m, 1H), 3.41-3.36 (m, 1H), 3.28-3.20 (m, 2H), 2.917-2.88 (m, 2H), 2.78 (s, 3H), 2.71-2.67 (m, 1H), 2.54-2.50 (m, 2H), 2.03-1.97 (m, 2H), 1.65-1.63 (m, 2H), 1.36-1.31 (m, 1H), 1.20-1.16 (m, 1H).

MS calculated value: 595; MS experimental value: 596 [M+H]⁺.

Synthesis of 2-((1S,3s)-3-(6-bromo-1-((R)-2-(2-methoxyphenyl)-2-((tetrahydro-2H-pyran-4-yl)oxy)ethyl)-5-methyl-2,4-dioxo-1,2-dihydrothieno[2,3-d]pyrimidine-3(4H)-yl)cyclobutyl)ethyl Acetate 2.81-2

Synthesis of 2-((1S,3s)-3-(1-((R)-2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidine-3(4H)-yl)cyclobutyl)ethyl Acetate 2.91-2

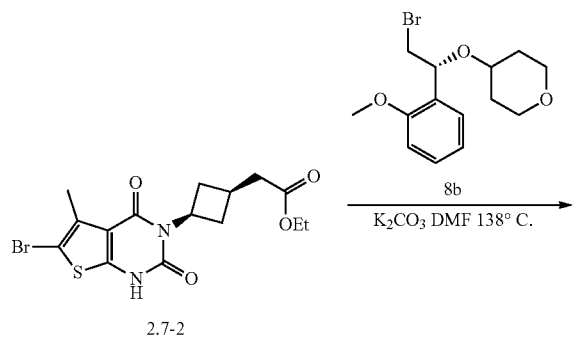

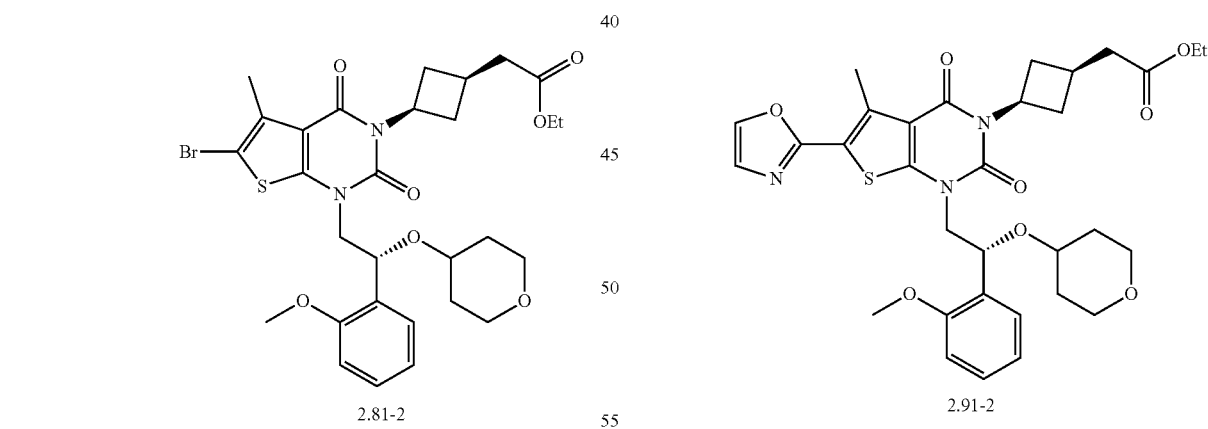

(R)-4-(2-bromo-1-(2-methoxyphenyl)ethyoxyl)tetrahydro-2H-pyrane 3.61 (3.2 g, 10 mmol) and $K_2CO_3$ (2 g, 14 mmol) were added to a solution of the compound 2.7-2 (2.0 g, 5.0 mmol) in DMF (20 mL). The reactants were stirred for 6 hours at 138° C. in an airtight tube, then cooled to room temperature, diluted with $H_2O$, and extracted with EA. Organic layers were combined, washed with saline, dried over $Na_2SO_4$, filtered and concentrated. The remains were purified by silica-gel flash chromatography (PE/EA=10/1) to obtain a compound 2.81-1 (3 g) as a colorless oil.

Mass spectrum: 637 [M+H]⁻

2-(tributylstannyl)oxazol (1.7 g, 4.7 mmol) and $Pd(PPh_3)_4$ (0.5 g, 0.4 mmol) were added to a solution of the compound 2.81-2 (1 g, 1.6 mmol) in toluene (20 mL). Then, the reaction mixture was stirred for 10 hours at 110° C. The reaction mixture was cooled to room temperature, diluted with $H_2O$, and extracted with EA. Organic layers were combined, washed with saline, dried over $Na_2SO_4$, filtered and concentrated. The remains were purified by silica-gel flash chromatography (PE/EA=3/1) to obtain a compound 2.91-2 (600 mg) as a yellow solid.

Mass spectrum: 624 [M+H]⁻

Synthesis of Compound 2-((1S,3s)-3-(1-((R)-2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidine-3(4H)-yl)cyclobutyl)acetic Acid c-3-2

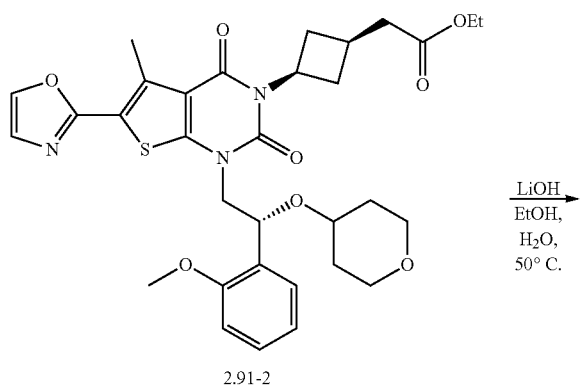

2.91-2

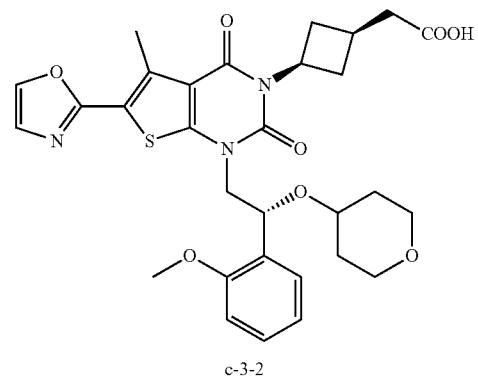

c-3-2

LiOH (338 mg, 8.0 mmol) was added to a solution of the compound 2.91-2 (1 g, 1.6 mmol) in EtOH (15 mL) and water (3 mL). The reaction mixture was stirred at 50° C. for 2 hours. The pH of the reaction mixture was adjusted to 7 with 5% HCl, and extracted with EA. Organic layers were combined, washed with saline, dried over $Na_2SO_4$, filtered and concentrated to obtain the remains, which were purified by silica-gel flash chromatography (DCM/MeOH=50/1) to obtain a compound c-3-2 (600 mg) as a white solid.

$^1$H NMR (400 MHz, DMSO-$d_6$) δ: 11.98 (br s, 1H), 8.22 (s, 1H), 7.50-7.48 (m, 1H), 7.38 (d, J=0.4 Hz, 1H), 7.32-7.27 (m, 1H), 7.05-6.97 (m, 2H), 5.30 (t, J=6.4 Hz, 1H), 5.13-5.04 (m, 1H), 4.11-4.00 (m, 2H), 3.78 (s, 3H), 3.61-3.57 (m, 1H), 3.53-3.48 (m, 1H), 3.41-3.35 (m, 1H), 3.28-3.20 (m, 2H), 2.78 (s, 3H), 2.50-2.45 (m, 3H), 2.43-2.31 (m, 4H), 1.66-1.62 (m, 2H), 1.38-1.31 (m, 1H), 1.23-1.15 (m, 1H).

MS calculated value: 595; MS experimental value: 596 [M+H]$^+$.

Example 8

Synthesis of 2-(tributylstannyl)oxazole 2-(tributylstannyl)oxazole was prepared by a method similar to that of Example 6.

Example 9

In Vitro Assay of Acetyl-CoA Carboxylase (ACC) Inhibition

An exemplary procedure for the in vitro ACC inhibition assay, which can be used to determine the inhibitory action of the compounds of the invention toward either ACC1 or ACC2, is as follows. The ADP-Glo™ kinase assay kit from Promega was used. The ADP-Glo™ kinase assay is a luminescent ADP detection assay to measure enzymatic activity by quantifying the amount of ADP produced during an enzyme reaction. The assay was performed in two steps; first, after the enzyme reaction, an equal volume of ADP-Glo™ reagent was added to terminate the reaction and deplete the remaining ATP. Then, the kinase detection reagent was added to simultaneously convert ADP to ATP and allow the newly synthesized ATP to be measured using a luciferase/luciferin reaction. Luminescence can be correlated to ADP concentrations by using an ATP-to-ADP conversion curve. The detailed procedure was as follows. 4.5 μL of a working solution was added to a 384-well plate. The compound was diluted at 1:3 in succession in DMSO. 0.5 μL of diluted compound solution was added to a 384-well white Optiplate assay plate. The plates were incubated at room temperature for 15 minutes. 5 μL of substrate working solution was added to each well to initiate the reaction. A final ACC reaction solution consisted of: 0.5 nM ACC, 10 μM ATP, 5 μM acetyl-CoA, and 15 mM $NaHCO_3$; and the final concentrations of the compound were measured as follows: 1 μM, 0.333 μM, 0.111 μM, 0.037 μM, 0.0123 μM, 0.00411 μM, 0.00137 μM, 0.000457 μM, 0.000152 μM, and 0.000051 μM. The plates were incubated at room temperature for 30 minutes. 10 μL of ADP-Glo™ reagent was added, and the plates were incubated at room temperature for 40 minutes. 20 μL of kinase detection reagent was added. The plates were incubated at room temperature for 40 minutes, then read on a Perkin Elmer EnVision 2104 plate reader for luminescence in relative light unit (RLU).

Data for each concentration, as well as the positive and negative controls were averaged, and the standard deviation was calculated. Percent inhibition was calculated by the formula: 100×(average negative control−compound)/(average negative control−average positive control). The $IC_{50}$ for each compound was calculated by fitting the data with a non-linear regression equation: Y=Bottom+(Top−Bottom)/(1+10^((Log $IC_{50}$−X)×HillSlope)), where X is the log of compound concentration and Y is the percent inhibition.

The exemplary results of the ACC1 and ACC2 inhibition assay in vitro are listed in Table 2. The compound numbers correspond to those listed in Table 1.

TABLE 2

Results of ACC1 and ACC2 inhibition assay in vitro

| Compound No. | Enzymatic activity $IC_{50}$ (μM) | |
| --- | --- | --- |
| | ACC1 | ACC2 |
| c-1 | 0.000487 | 0.010 |
| c-3 | 0.000688 | 0.003 |

TABLE 2-continued

Results of ACC1 and ACC2 inhibition assay in vitro

| Compound No. | Enzymatic activity IC$_{50}$ (μM) | |
| --- | --- | --- |
|  | ACC1 | ACC2 |
| c-3-1 | 0.000836 | 0.009 |
| c-3-2 | 0.001124 | 0.008 |

It can be known from the table that the compounds c-1, c-3, c-3-1, and c-3-2 show good inhibitory properties against ACC1 and ACC2. All other compounds of the present invention have a good inhibitory activity against ACC1 and ACC2, showing equivalent IC$_{50}$ values against ACC1 and ACC2 as those of the compounds c-1 and c-3.

Example 10

[2-$^{14}$C]-Acetate Incorporation Assay in HepG2 Cells

Complete Culture Medium:
DMEM (GIBCO, catalog number: 11965-092) was used as a complete culture medium for HepG2 cells (ATCC, catalog number: HB-8064). 10% fetal bovein serum (FBS, GIBCO, catalog number: 10099-141), penicillin (100 units/mL) and streptomycin (100 μg/mL) (Pen/Strep, GIBCO, catalog number: 15140-122) were added to a DMEM culture medium.

Cell Culture Condition:
HepG2 cells were cultured in a 37° C. incubator holding 5% carbon dioxide, and passaged every 2-3 days.

[2-$^{14}$C]-Acetate Binding Assay:
The HepG2 cells were spread on a 24-well plate (Corning, catalog number: 3524) at a density of 2×10$^5$ cells-well, 500 μL per well, and cultured in a 37° C. incubator holding 5% carbon dioxide. On the fourth day of culture, 50 μL of a compound diluted at a gradient of 1:3 was added, with the final concentration of DMSO of 0.5% (v/v); and the cells were cultured for 1 hour in the incubator. 1 μCi [2-$^{14}$C]-sodium acetate (Perkin Elmer, catalog number: NEC085H001MC) was added to each well, and culture was conducted for another 5 hours. The culture medium in each well was transferred to a 15 mL centrifugal tube (BD, catalog number: 352096); 0.5 mL of 0.1 M NaOH was added; the cells were blown and washed repeatedly, and then transferred to new centrifugal tubes. Then, 1 mL of ethanol and 0.17 mL of 50% KOH solution were added to each centrifugal tube, which was then treated in a water bath at 90° C. for 1 hour. Next, the mixture was cooled to room temperature; 5 mL of petroleum ether was added to each centrifugal tube, which was turned upside down several times for mixing; the resulting mixture was centrifuged for 5 minutes (Eppendorf, Model: 5702, 1000 rpm); and an upper organic phase was discarded. 1 mL of concentrated hydrochloric acid was added to each centrifugal tube and centrifuged for 5 minutes, and 4 mL of petroleum ether was transferred into a glass tube (18×180 mm). The sample in the glass tube was dried at 64° C., and then dissolved and resuspended by addition of 400 μL of spotting solution (chloroform:n-hexane=1:1). 50 μL of the dissolved sample was drawn by a pipette (BIOHIT, Model: Proline Plus), and spotted onto an Isoplate-96-microwell plate (Perkin Elmer, catalog number: 6005040), and 200 μL of ULTIMA GOLD scintillation solution (Perkin Elmer, catalog number: 77-16061) was added, standing for 5 minutes. Finally, MicroBeta (PerkinElmer, Model: 2450) was used to read scintillation signals.

Data Analysis:
A 4-parameter logistic model or sigmoidal dose-response model in XLFit 5.3.1.3 (2006-2011 I D Business Solutions Limited) was used to fit IC$_{50}$: fit=(A+((B−A)/(1+((C/x)^D)))); where the x-axis represented the log of compound concentration, and the y-axis represented count per minute (CPM).

The exemplary results of the [2-$^{14}$C]-acetate binding assay are listed in Table 3. The compound numbers correspond to those listed in Table 1.

TABLE 3

Results of [2-$^{14}$C]-acetate binding assay.

| Compound No. | IC$_{50}$ (μM) |
| --- | --- |
| c-1 | 0.2317 |
| c-3 | 0.0185 |
| c-3-1 | 0.0131 |
| c-3-2 | 0.0180 |

It can be own om a e that the compounds, m particular compounds c-3, c-3-1 and c-3-2, listed in the table above, have good inhibitory properties against HepG2 cells. All other compounds of the present invention have a good inhibitory activity against HepG2 cells, showing equivalent IC$_{50}$ values as those of the compounds c-3, c-3-1 and c-3-2.

Example 11

Pharmacokinetic Evaluation of Compounds in Rats

This example was intended to investigate the pharmacokinetics of the compounds of the present invention and ND630 in SD rats under the conditions of intravenous (iv) and intragastric administration (po). Unless otherwise stated, the experimental reagents and instruments are all commercially available. ND630 was Gilead's acetyl CoA carboxylase (ACC) inhibitor, with a structural formula as follows:

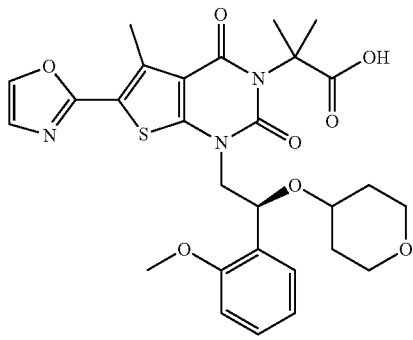

Formulation of compound: by taking a physiological saline solution of 5% DMSO+5% Solutol HS 15+90% HP-β-CD (20% w/v) as a solvent, a compound with the final concentration of 0.4 mg/mL was formulated for intravenous administration and a compound with the final concentration of 1 mg/mL was formulated for orally intragastric administration.

Animal feeding and management: male SD rats aged 6-8 weeks and weighing between 180-250 g were selected and raised in transparent resin plastic rate cages. Before administration, the rats were fasted overnight for at least 16 hours, and the feed supply was restored 4 hours after administration.

For the intravenous injection administration group, the dose was 2 mg/kg, and 0.2 mL of blood samples was collected from the jugular vein 5 min, 15 min, 30 min, 1 h, 3 h, 5 h, and 8 h after dosage. For the orally intragastric administration group, the dose was 10 mg/kg, and 0.2 mL of blood samples was collected from the jugular vein 15 min, 30 min, 1 h, 3 h, 5 h, 8 h, 12 h, and 24 h after dosage; and liver tissues were collected 1 h, 3 h and 24 h after dosage.

After the blood were sampled, the plasma was quickly separated by centrifugation at 4000 rpm (10 minutes, 4° C.). After the liver tissues were sampled, a mixture of methanol:water (1:1, v/v) three times the volume of the liver tissues was added to prepare a homogenate. 50 μL of plasma or homogenate sample was drawn, and 200 μL of an internal standard (30 ng/mL terfenadine, and acetonitrile) was added for precipitation. Centrifuging was carried out at 4° C. and 15,400 g for 10 minutes, and a supernatant was taken for analysis.

The concentration of a target compound was detected by LC-MS/MS. According to the plasma concentration-time curve, pharmacokinetic parameters were calculated by using a non-compartmental model (NCA) of software WinNonlin 7.0. The pharmacokinetic properties of representative compounds are listed in Table 4 below. The analysis results show that the compounds the present invention show good pharmacokinetic properties, for example, high bioavailability F (%), high exposure (AUC), high liver-to-blood ratio (L/P), etc. Table 4. Pharmacokinetic results F %: bioavailability $C_{max}$: maximum plasma concentration after one dosage $T_{max}$: time to reach maximum plasma concentration AUC: area below plasma concentration-time curve, drug uptake $t_{1/2}$: half-life period Vss: volume of steady-state performance distribution Cl blood drug clearance

| Compound No. | ND630 | c-3-1 | c-3-2 |
|---|---|---|---|
| F (%) | 35.8 | 99.6 | 62.3 |
| $C_{max}$ (ng/mL) | 5628 (iv) | 4100 (iv) | 3113) (iv) |
|  | 2882 (po) | 7780 (po) | 3243 (po) |
| $T_{max}$ (h) | 0.083 (iv) | 0.0833 (iv) | 0.0833 (iv) |
|  | 0.4 (po) | 0.5 (po) | 0.4 (po) |
| $AUC_{0-\infty}$ (ng·h/mL) | 2871 (iv) | 3119 (iv) | 1386 (iv) |
|  | 5093 (po) | 15688 (po) | 4353 (po) |
| $t_{1/2}$ (h) | 1.06 (iv) | 1.74 (iv) | 0.9 (iv) |
|  | 0.65 (po) | 4.65 (po) | 4.82 (po) |
| Vss (mL/kg) | 480 | 826 | 839 |
| Cl (mL/h/g) | 735 | 642 | 1503 |
| L/P | 5.5-41.9 | 9.46-17.3 | 20.6-30.0 |

The invention claimed is:

1. A compound of formula c:

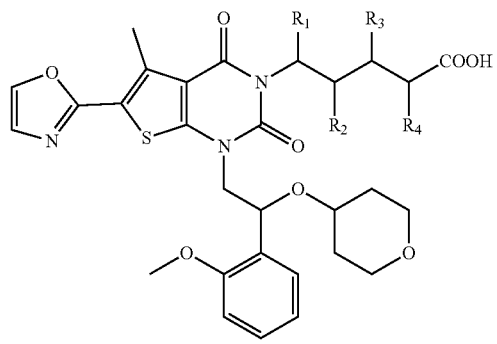

or a pharmaceutically acceptable salt thereof, wherein, $R_1$ is H, $C_{1-6}$ alkyl, $C_{1-6}$ haloalkyl, or $C_{1-6}$ alkoxy;

$R_2$ is H, $C_{1-6}$ alkyl, $C_{1-6}$ haloalkyl, or $C_{1-6}$ alkoxy;

$R_3$ is H, $C_{1-6}$ alkyl, $C_{1-6}$ haloalkyl, or $C_{1-6}$ alkoxy, or $R_1$ and $R_3$, together with a carbon atom bonded thereto, form 3-6 membered cycloalkyl; and $R_4$ is H, $C_{1-6}$ alkyl, $C_{1-6}$ haloalkyl, or $C_{1-6}$ alkoxy, or $R_4$ and $R_2$, together with a carbon atom bonded thereto, form 3-6 membered cycloalkyl.

2. The compound according to claim 1, wherein $R_2$ and $R_4$ are each independently H, and $R_1$ and $R_3$ form a four-membered ring.

3. The compound according to claim 1, wherein $R_1$ and $R_3$ are each independently H, and $R_2$ and $R_4$ form a four-membered ring.

4. The compound according to claim 1, wherein the compound is selected from the group consisting of:

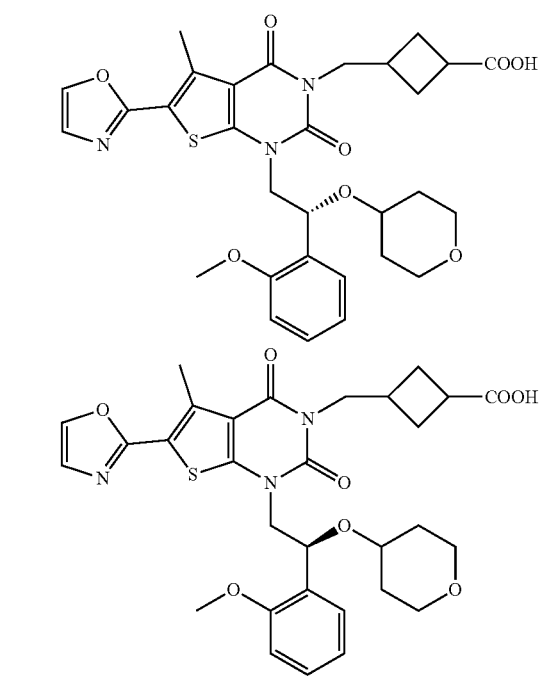

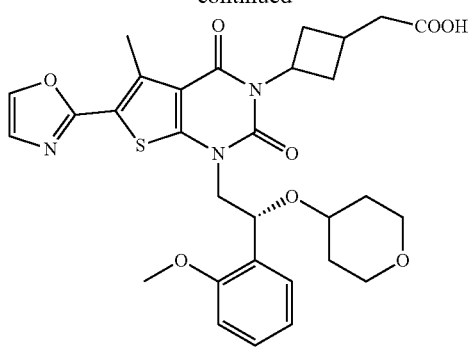

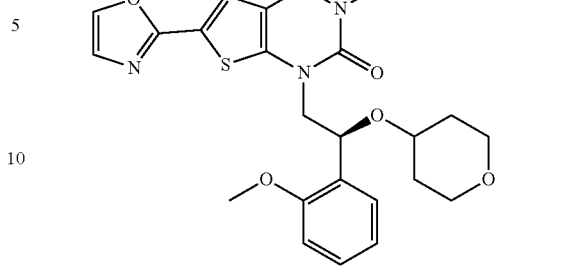

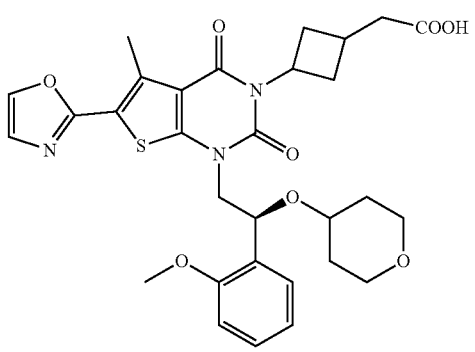 [SMILES: COc1ccccc1[C@@H](Cn1c(=O)n(C2CC(CC(=O)O)C2)c(=O)c2c(C)c(-c3ncco3)sc21)OC1CCOCC1]

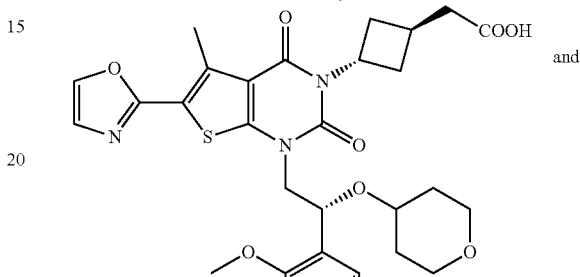

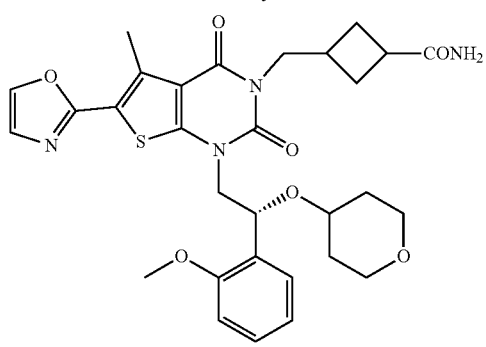

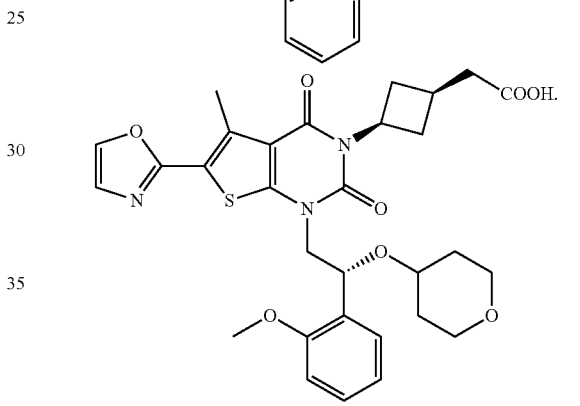

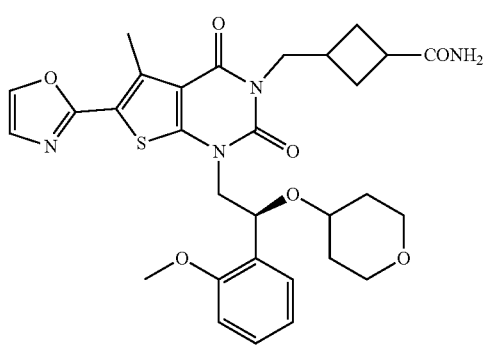

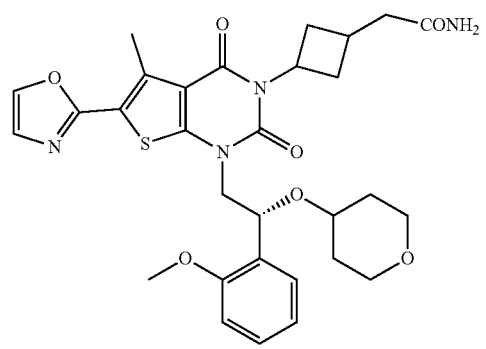 [SMILES: COc1ccccc1[C@H](Cn1c(=O)n(C2CC(CC(N)=O)C2)c(=O)c2c(C)c(-c3ncco3)sc21)OC1CCOCC1]

5. A composition which comprises the compound of formula c or a pharmaceutically acceptable salt thereof according to claim 1.

6. The composition according to claim 5, wherein the composition is a pharmaceutical composition.

7. The composition according to claim 6, wherein the composition further comprises a pharmaceutically acceptable carrier.

8. The composition according to claim 5, wherein the formulation of the composition is an oral preparation or intravenous preparation.

9. A method for (a) inhibiting acetyl-CoA carboxylase; (b) treating disorders mediated by ACC; (c) treating a metabolic disease; (d) treating a cancer or other proliferative disorders; and/or (e) treating non-alcoholic steatohepatitis; which the method comprises administering the compound of formula c or a pharmaceutically acceptable salt thereof according to claim 1 or the composition according to claim 5 to a patient.

10. The method according to claim 9, wherein the acetyl-CoA carboxylase is selected from group consisting of acetyl-CoA carboxylase 1, acetyl-CoA carboxylase 2, and combinations therefore.

11. The method according to claim 9, wherein the metabolic disease is obesity, dyslipidemia or hyperlipidemia.

12. The method according to claim 9, wherein the cancer is selected from group consisting of liver cancer, cholangiocarcinoma, angiosarcoma, hemangiosarcoma, melanoma, liposarcoma, lung cancer, breast cancer, prostate cancer, leukemia, kidney cancer, esophageal cancer, brain cancer, lymphoma, colon cancer, and combinations therefore.

13. The method according to claim 12, wherein the liver cancer cell is HepG2 cell.

* * * * *